United States Patent
Onuma

(10) Patent No.: US 10,631,919 B2
(45) Date of Patent: Apr. 28, 2020

(54) ENERGY TREATMENT INSTRUMENT

(71) Applicant: OLYMPUS CORPORATION, Hachioji-shi, Tokyo (JP)

(72) Inventor: Ryu Onuma, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 732 days.

(21) Appl. No.: 15/394,192

(22) Filed: Dec. 29, 2016

(65) Prior Publication Data

US 2017/0105790 A1   Apr. 20, 2017

Related U.S. Application Data

(63) Continuation of application No. PCT/JP2015/066614, filed on Jun. 9, 2015.

(30) Foreign Application Priority Data

Jul. 10, 2014   (JP) .................................. 2014-142633

(51) Int. Cl.
*A61B 18/14*   (2006.01)
*A61B 17/32*   (2006.01)
(Continued)

(52) U.S. Cl.
CPC .. *A61B 18/1445* (2013.01); *A61B 17/320092* (2013.01); *A61B 18/00* (2013.01); *A61B 18/12* (2013.01); *A61B 2017/320093* (2017.08); *A61B 2017/320095* (2017.08); *A61B 2018/00029* (2013.01); *A61B 2018/00404* (2013.01);

(Continued)

(58) Field of Classification Search
CPC combination set(s) only.
See application file for complete search history.

(56) References Cited

U.S. PATENT DOCUMENTS

| 5,417,709 A | 5/1995 | Slater |
| 6,340,352 B1 * | 1/2002 | Okada ............ A61B 17/320092 |
| | | 601/2 |

(Continued)

FOREIGN PATENT DOCUMENTS

| JP | 2002-000614 A | 1/2002 |
| JP | 2005-237574 A | 9/2005 |

(Continued)

OTHER PUBLICATIONS

Feb. 14, 2018 Partial Supplementary European Search Report issued in Patent Application No. 15818717.9.

(Continued)

*Primary Examiner* — Jaymi E Della
(74) *Attorney, Agent, or Firm* — Oliff PLC

(57) ABSTRACT

In an energy treatment unit and an energy treatment instrument, a jaw openable and closable relative to a probe distal portion of a probe is attached to a distal portion of an energy transmission portion. A liquid feed conduit extends between the energy transmission portion and the probe in a cavity portion, and a liquid ejected from an ejection port, that is formed at a distal end of the liquid feed conduit, flows into a jaw cavity in an inside of the jaw. A liquid outflow portion is provided on an outer surface of the jaw, and the liquid flowing into the jaw cavity flows to an outside of the jaw from the liquid outflow portion.

14 Claims, 9 Drawing Sheets

(51) Int. Cl.
  *A61B 18/12* (2006.01)
  *A61B 18/00* (2006.01)
(52) U.S. Cl.
  CPC .............. *A61B 2018/00589* (2013.01); *A61B 2018/00994* (2013.01); *A61B 2217/005* (2013.01); *A61B 2217/007* (2013.01); *A61B 2218/002* (2013.01); *A61B 2218/003* (2013.01); *A61B 2218/007* (2013.01)

(56) References Cited

U.S. PATENT DOCUMENTS

| | | | |
|---|---|---|---|
| 7,621,910 | B2 | 11/2009 | Sugi |
| 9,044,261 | B2 | 6/2015 | Houser |
| 2005/0187547 | A1 | 8/2005 | Sugi |
| 2009/0036914 | A1 | 2/2009 | Houser |
| 2009/0270853 | A1* | 10/2009 | Yachi ............. A61B 17/320092 606/27 |
| 2010/0185197 | A1 | 7/2010 | Sakao et al. |
| 2011/0230880 | A1* | 9/2011 | Chojin ............... A61B 18/1445 606/45 |
| 2012/0170855 | A1 | 7/2012 | Maeda |
| 2013/0116686 | A1 | 5/2013 | Akagane |
| 2013/0218185 | A1* | 8/2013 | Sanai ............. A61B 17/320092 606/169 |
| 2014/0025058 | A1* | 1/2014 | Winkler ............. A61B 18/1482 606/33 |
| 2014/0188014 | A1 | 7/2014 | Akagane |

FOREIGN PATENT DOCUMENTS

| | | |
|---|---|---|
| JP | 2010-535087 A | 11/2010 |
| WO | 2004/026104 A2 | 4/2004 |
| WO | 2012/011213 A1 | 1/2012 |
| WO | 2012/121213 A1 | 9/2012 |

OTHER PUBLICATIONS

Jun. 4, 2018 Extended European Search Report issued in Patent Application No. 15818717.9.
Aug. 25, 2015 International Search Report issued in Patent Application No. PCT/JP2015/066614.
May 17, 2016 Office Action issued in Japanese Patent Application No. 2016-504408.
Oct. 4, 2016 Office Action issued in Japanese Patent Application No. 2016-504408.
Jan. 10, 2017 International Preliminary Report on Patentability issued in Patent Application No. PCT/JP2015/066614.

* cited by examiner

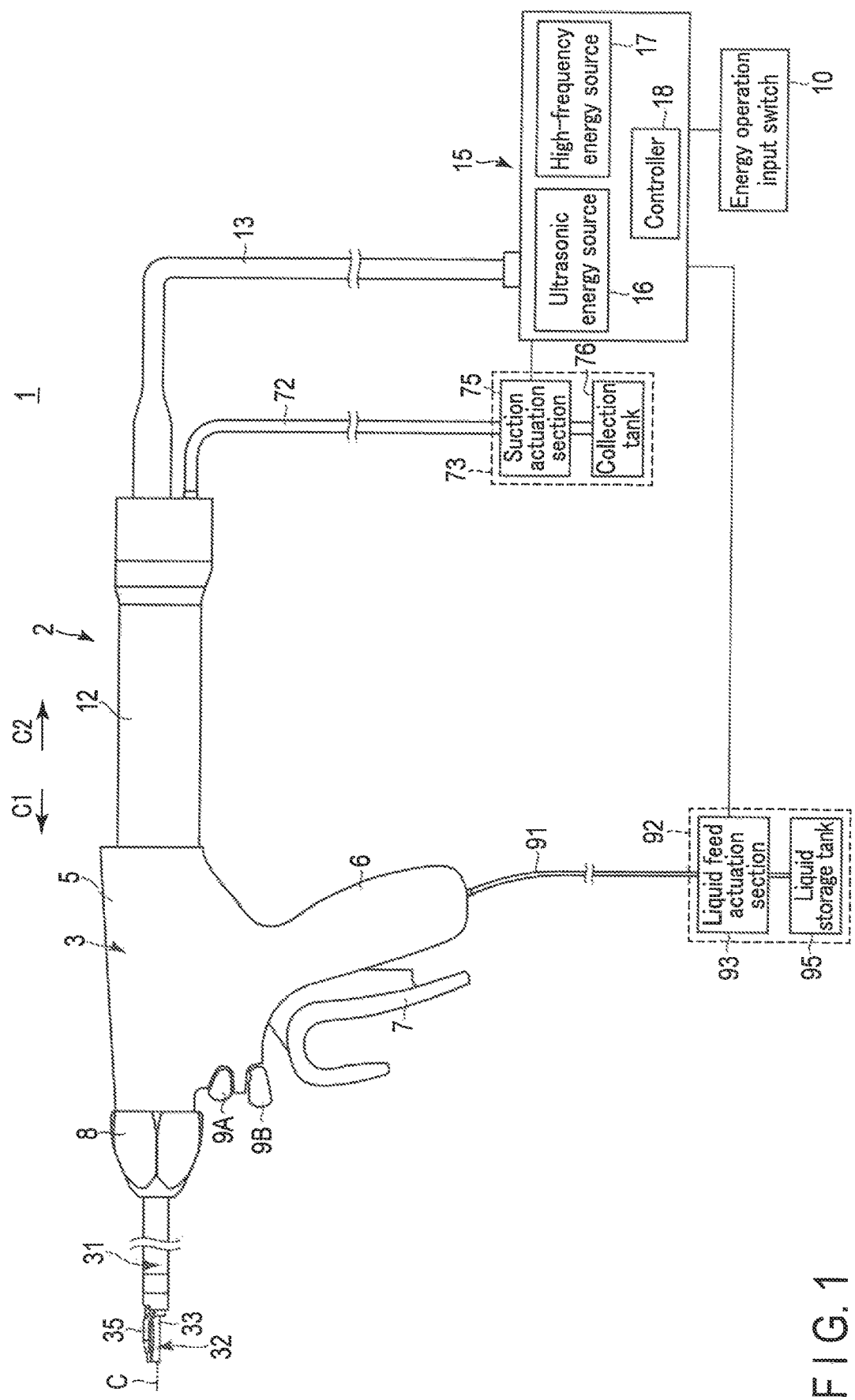
F I G. 1

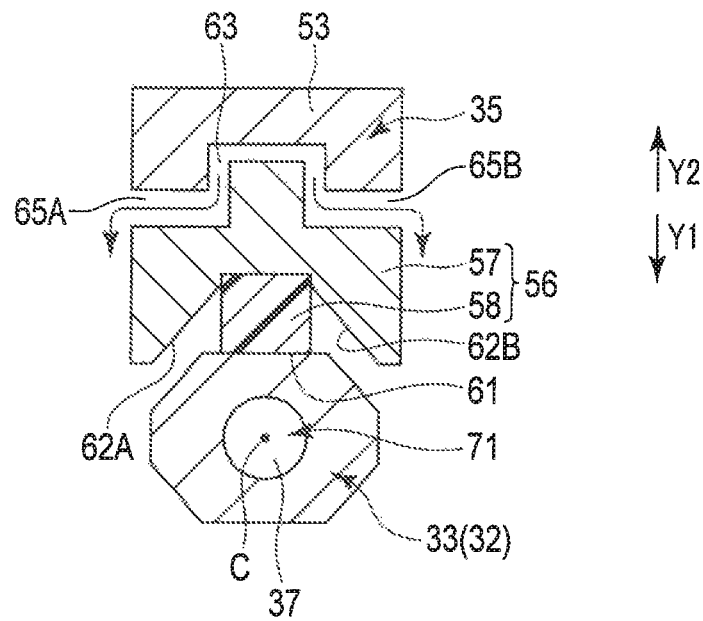
F I G. 4
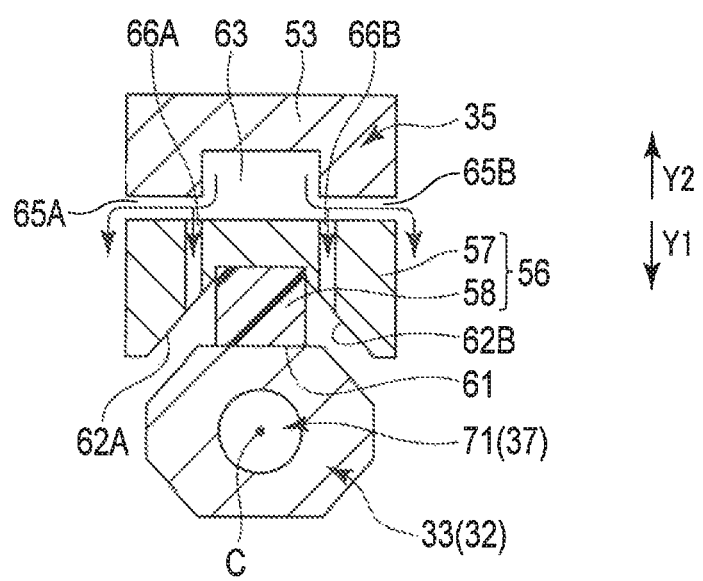
F I G. 5

ENERGY TREATMENT INSTRUMENT

CROSS-REFERENCE TO RELATED APPLICATIONS

This is a Continuation Application of PCT Application No. PCT/JP2015/066614, filed Jun. 9, 2015 and based upon and claiming the benefit of priority from prior Japanese Patent Application No. 2014-142633, filed Jul. 10, 2014, the entire contents of which are incorporated herein by reference.

BACKGROUND OF THE INVENTION

1. Field of the Invention

The present invention relates to an energy treatment unit which is used together with a probe and includes a jaw which is openable and closable relative to a probe distal portion (treatment section) of a probe, and relates to an energy treatment instrument including the energy treatment unit.

2. Description of the Related Art

PCT International Publication No. 2004/026104 discloses an energy treatment instrument including a probe which transmits ultrasonic vibration from a proximal direction side to a distal direction side, and a treatment unit which is used together with the probe. The treatment unit includes a sheath through which the probe is inserted, and a jaw (grasping unit) which is attached to a distal portion of the sheath. A probe distal portion (treatment section) of the probe projects from a distal end of the sheath toward a distal direction. The jaw is openable and closable relative to the probe distal portion. In addition, a liquid feed tube (irrigation tube) extends in a cavity portion between the sheath and the probe from the proximal direction side toward the distal direction side. A liquid feed conduit is formed in an inside of the liquid feed tube. The liquid feed tube is movable along a longitudinal axis relative to the probe and sheath. An ejection port, which is formed at a distal end of the liquid feed conduit, is located on an outer surface of the probe distal portion.

BRIEF SUMMARY OF THE INVENTION

According to one aspect of the invention, an energy treatment unit which is used together with a probe, including: an energy transmission portion including a distal end and a proximal end, and configured to transmit energy, which is used for a treatment, from a proximal direction side toward a distal direction side, the energy transmission portion being configured such that a cavity portion, through which the probe is inserted, is formed in an inside of the energy transmission portion along a longitudinal axis; a jaw attached to a distal portion of the energy transmission portion, and configured such that a jaw cavity is formed in an inside of the jaw, the jaw being configured to open and close relative to a probe distal portion of the probe, the probe distal portion projecting from the distal end of the energy transmission portion toward the distal direction side; a liquid feed conduit extending from the proximal direction side toward the distal direction side, through between the energy transmission portion and the probe in the cavity portion, the liquid feed conduit being configured such that an ejection port is formed at a distal end of the liquid feed conduit, and configured to eject a supplied liquid from the ejection port toward the distal direction side and to cause the ejected liquid to flow into the jaw cavity; and a liquid outflow portion located on an outer surface of the jaw, and configured to cause the liquid flowing into the jaw cavity to flow to an outside of the jaw.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view illustrating an energy treatment system according to a first embodiment;

FIG. 4 is a cross-sectional view taken along line IV-IV in FIG. 3;

FIG. 5 is a cross-sectional view taken along line V-V in FIG. 3;

DETAILED DESCRIPTION OF THE INVENTION

First Embodiment

Figure 2:
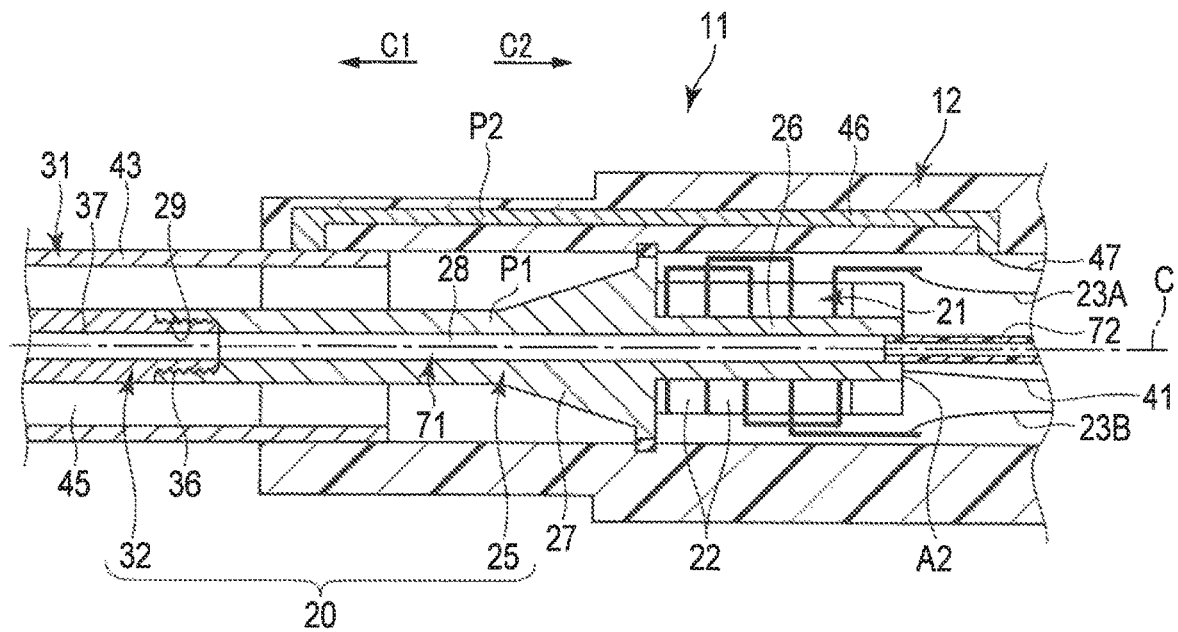
FIG. 2 is a cross-sectional view which schematically illustrates the configuration of a transducer unit according to the first embodiment, and the vicinity of the transducer unit.

A first embodiment of the present invention will be described with reference to FIG. 1 to FIG. 6.

FIG. 1 is a view illustrating the configuration of an energy treatment system 1 of the present embodiment. As illustrated in FIG. 1, the energy treatment system 1 includes an energy treatment instrument (handpiece) 2. The energy treatment instrument 2 has a longitudinal axis C. Here, two directions parallel to the longitudinal axis C are set as longitudinal directions. One of the longitudinal directions is a distal direction (a direction of arrow C1 in FIG. 1), and the direction opposite to the distal direction is a proximal direction (a direction of arrow C2 in FIG. 1). In this embodiment, the energy treatment instrument 2 is an ultrasonic treatment instrument which treats a treated target, such as a biological tissue, by using ultrasonic vibration as energy, and is also a high-frequency treatment instrument which treats the treated target by using high-frequency electric power (high-frequency current) as energy.

The energy treatment instrument 2 includes a holding unit (handle unit) 3. The holding unit 3 includes a cylindrical case portion 5 which extends along the longitudinal axis C, and a stationary handle 6 which extends from the cylindrical case portion 5 in a certain direction crossing the longitudinal axis C. The cylindrical case portion 5 and stationary handle 6 are formed as one body. A movable handle 7 is rotatably attached to the cylindrical case portion 5. By the movable handle 7 rotating about the position of attachment to the cylindrical case portion 5, the movable handle 7 opens or closes relative to the stationary handle 6. In the present embodiment, the movable handle 7 is located on the distal direction side with respect to the stationary handle 6. In addition, the holding unit 3 includes a rotary operation knob 8 which is a rotary operation input section that is attached to a distal direction side of the cylindrical case portion 5, and the rotary operation knob 8 is provided coaxial with the longitudinal axis C. The rotatable operation knob 8 is rotatable about the longitudinal axis C relative to the cylindrical case portion 5.

In addition, energy operation input buttons 9A and 9B, which are energy operation input sections, are attached to the cylindrical case portion 5 of the holding unit 3. The energy operation input buttons 9A and 9B are located on the side where the stationary handle 6 is located, with reference to the longitudinal axis C as the center. Besides, in this embodiment, the energy operation input buttons 9A and 9B are located on the distal direction side with respect to the stationary handle 6.

The energy treatment instrument 2 includes a transducer unit 11. The transducer unit 11 includes a transducer case 12. The transducer case 12, integral with the rotary operation knob 8, is rotatable about the longitudinal axis C relative to the cylindrical case portion 5. The transducer case 12 is attached to the holding unit 3, by the transducer case 12 being inserted into the inside of the cylindrical case portion 5 from the proximal direction side. One end of a cable 13 is connected to the transducer case 12. The energy treatment system 1 includes an energy source unit 15 which is, for example, an energy control device. The other end of the cable 13 is connected to the energy source unit 15. In the present embodiment, the energy source unit 15 includes an ultrasonic energy source 16, a high-frequency energy source 17, and a controller 18. The ultrasonic energy source 16 and high-frequency energy source 17 include, for example, converter circuits which convert electric power from an electric power supply to energy. The controller 18 is composed of a processor which includes, for example, a CPU (Central Processing Unit) or an ASIC (Application Specific Integrated Circuit), and a storage medium such as a memory. In addition, the energy source unit 15 is electrically connected to an energy operation input switch 10 such as a footswitch, which is an energy operation input section.

FIG. 2 is a view illustrating the configuration of the transducer unit 11 and the vicinity of the transducer unit 11. As illustrated in FIG. 2, the transducer unit 11 includes an ultrasonic transducer 21 which is a vibration generating section that is provided in the inside of the transducer case 12. The ultrasonic transducer 21 includes a plurality (for example, four in this embodiment) of piezoelectric elements 22 which convert an electric current (AC current) to ultrasonic vibration. One end of each of electric wiring portions 23A and 23B is connected to the ultrasonic oscillator 21. The electric wiring portions 23A and 23B extend through the inside of the oscillator case 12 and the inside of the cable 13, and the other ends of the electric wiring portions 23A and 23B are connected to the ultrasonic energy source 16 of the energy source unit 15. Ultrasonic electric power (ultrasonic electric energy) is supplied from the ultrasonic energy source 16 to the ultrasonic transducer 21 via the electric wiring portions 23A and 23B, and thereby ultrasonic vibration is generated by the ultrasonic transducer 21. In addition, by the supply of ultrasonic electric power (AC current), ultrasonic vibration is caused by the ultrasonic transducer 21 as energy that is used for a treatment.

The ultrasonic transducer 21 is attached to a cylindrical horn member 25. The ultrasonic transducer 21, which includes the piezoelectric elements 22, is fixed to an outer peripheral surface of an elements-attached portion 26 of the horn member 25. In addition, in the horn member 25, a cross-sectional area varying portion 27 is provided on a distal direction side with respect to the elements-attached portion 26. The cross-sectional area varying portion 27 has a cross-sectional area perpendicular to the longitudinal axis C, which gradually decreases toward the distal direction. The ultrasonic vibration, which is generated by the ultrasonic transducer 21, is transmitted to the horn member 25, and is transmitted in the horn member 25 from the proximal direction to the distal direction. The amplitude of the ultrasonic vibration, which is transmitted to the horn member 25, is increased in the cross-sectional area varying portion 27. In addition, since the horn member 25 is formed in the cylindrical shape, a cavity portion 28 is formed in the inside of the horn member 25. The cavity portion 28 extends along the longitudinal axis C from a proximal end of the horn member 25 to a distal end of the horn member 25. Besides, a female screw portion 29 is formed in a distal portion of the horn member 25.

As illustrated in FIG. 1, the energy treatment instrument 2 includes a sheath 31 which extends along the longitudinal axis C. The sheath 31 is attached to the holding unit 3, by the sheath 31 being inserted into the inside of the rotary operation knob 8 and the inside of the cylindrical case portion 5 from the distal direction side. In the inside of the cylindrical case portion 5, the sheath 31 is attached to a distal direction side of the transducer case 12. In this embodiment, the longitudinal axis C agrees with the center axis of the sheath 31.

In addition, the energy treatment instrument 2 includes a probe (ultrasonic probe) 32 which is inserted through the sheath 31. The probe 32 extends along the longitudinal axis C toward the distal direction from the inside of the holding unit 3 (the inside of the cylindrical case portion 5) through the inside of the sheath 31. In this embodiment, the longitudinal axis C agrees with the center axis of the probe 32. The probe 32 includes a probe proximal portion and a probe distal portion 33 that is a treatment section, and extends along the longitudinal axis C from a probe proximal portion direction toward a probe distal portion direction. Here, a direction toward the probe distal portion 33 in the probe 32 is the probe distal portion direction, and a direction toward the probe proximal portion in the probe 32 is the probe proximal portion direction. In the present embodiment, the probe distal portion direction agrees with the above-described distal direction, and the probe proximal portion direction agrees with the above-described proximal direction. The probe distal portion (treatment section) 33 projects from a distal end of the sheath 31 toward the distal direction (probe distal portion direction).

In addition, a jaw 35, which is a grasping unit, is rotatably attached to a distal portion of the sheath 31. By the jaw 35 rotating relative to the sheath 31, the jaw 35 opens or closes relative to the probe distal portion 33. Specifically, the jaw 35 is openable and closable relative to the probe distal portion 33. The sheath 31, probe 32 and jaw 35 can rotate, integral with the rotary operation knob 8, about the longitudinal axis C relative to the cylindrical case portion 5.

As illustrated in FIG. 2, a male screw portion 36 is formed on a probe proximal portion (proximal portion) of the probe 32. The male screw portion 36 is engaged with the female screw portion 29 of the horn member 25, and thereby the probe 32 is connected to a distal direction side of the horn member 25. The probe 32 is connected to the horn member 25 in the inside of the cylindrical case portion 5 of the holding unit 3.

Figure 3:
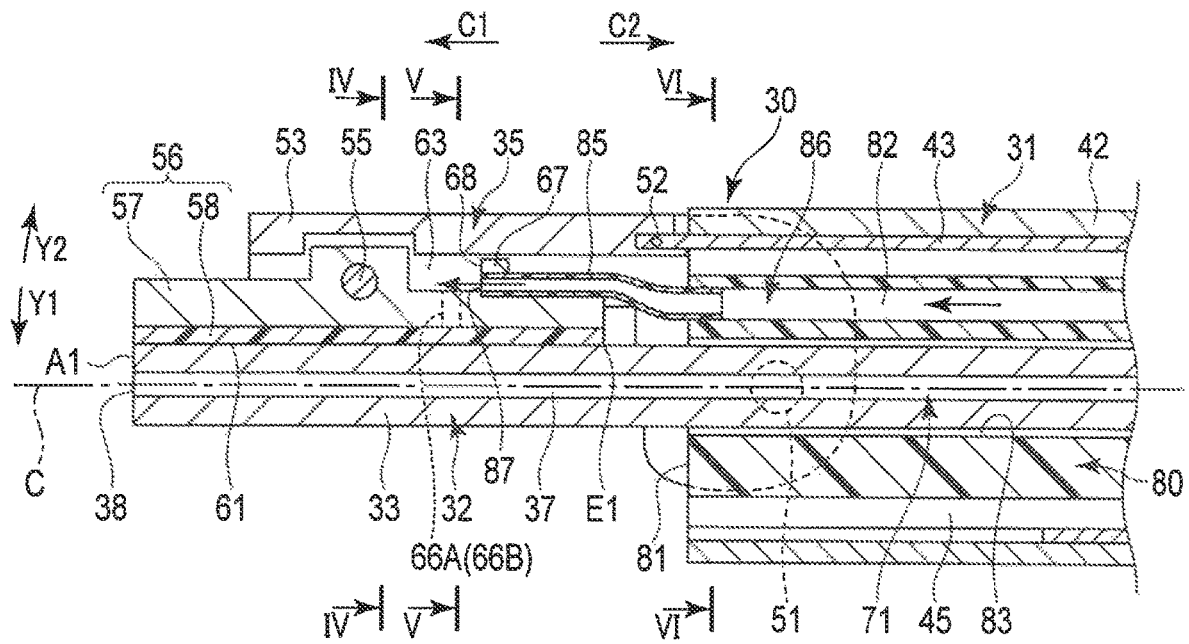
FIG. 3 is a cross-sectional view which schematically illustrates the configuration of a distal portion of an energy treatment instrument including a probe distal portion and a jaw according to the first embodiment.

FIG. 3 is a view illustrating the configuration of a distal portion (a distal-direction-side part) of the energy treatment instrument 2 including the probe distal portion (treatment section) 33 and the jaw 35. As illustrated in FIG. 2 and FIG. 3, a hollow portion 37 is formed along the longitudinal axis C in the inside of the probe 32. The hollow portion 37 extends from the probe proximal portion of the probe 32 to the probe distal portion (treatment section) 33 of the probe 32. The hollow portion 37 is open to the outside of the probe 32 by an opening portion 38 which is located on an outer surface (a distal surface in the embodiment) of the probe distal portion 33. The opening portion 38 establishes communication between the hollow portion 37 in the inside of the probe 32 and the outside of the probe 32. In the state in which the probe 32 is connected to the horn member 25, a proximal end of the hollow portion 37 communicates with a distal end of the cavity portion 28 which extends in the inside of the horn member 25.

Vibration, which has been transmitted from the ultrasonic transducer 21 to the horn member 25, is transmitted to the probe 32. In addition, the probe 32, which is the ultrasonic probe, transmits the ultrasonic vibration, which is energy, from a probe proximal portion direction side (proximal direction side) to a probe distal portion direction side (distal direction side). Then, the probe distal portion (treatment section) 33 performs a treatment by using the transmitted ultrasonic vibration. In this case, the horn member 25 and probe 32 form a vibrating body unit 20 which transmits the ultrasonic vibration, which was generated by the ultrasonic transducer 21, and vibrates by the ultrasonic vibration.

By the vibrating body unit 20 transmitting the ultrasonic vibration caused by the ultrasonic transducer 21, the vibrating body unit 20 vibrates in a preset vibration mode (vibration state) which is used at a time of treatment. In the preset vibration mode, the vibrating body unit 20 performs longitudinal vibration, the vibration direction of which is parallel to the longitudinal axis C (longitudinal direction). In addition, in the preset vibration mode, a distal end of the vibrating body unit 20 (a distal end of the probe 32) and a proximal end of the vibrating body unit 20 (the proximal end of the horn member 25) become antinode positions of the longitudinal vibration. Here, an antinode position A1, which is located at the distal end of the vibrating body unit 20, is located most on the probe distal portion direction side among the antinode positions of longitudinal vibration, and an antinode position A2, which is located at the proximal end of the vibrating body unit 20, is located most on the probe proximal portion direction side among the antinode positions of longitudinal vibration. In addition, in the established vibration mode, the number of antinode positions of longitudinal vibration and the number of node positions of longitudinal vibration between the distal end of the vibrating body unit 20 and the proximal end of the vibrating body unit 20 are fixed, and at least one node position of longitudinal vibration exists between the distal end of the vibrating body unit 20 and the proximal end of the vibrating body unit 20. The controller 18 adjusts the frequency of an electric current (AC current) which is supplied from the ultrasonic energy source 16 to the ultrasonic transducer 21, thereby adjusting the resonance frequency of the vibrating body unit 20 and causing the vibrating body unit 20 to longitudinally vibrate in the preset vibration mode. In the meantime, the preset vibration mode (i.e. the number of node positions and antinode positions of longitudinal vibration, and the locations of node positions and antinode portions in the longitudinal direction) is determined in accordance with the dimension in the longitudinal direction of the used vibrating body unit 20, the kind of treatment, etc.

In addition, one end of an electric wiring portion 41 is connected to the horn member 25. The other end of the electric wiring portion 41 is electrically connected to the high-frequency energy source 17 of the energy source unit 15. The electric wiring portion 41 extends through the inside of the transducer case 12 and the inside of the cable 13. The high-frequency energy source 17 outputs high-frequency electric power (high-frequency electric energy) as energy that is used for a treatment. The high-frequency electric power, which is output from the high-frequency energy source 17, is supplied to the probe distal portion (treatment section) 33 through the electric wiring portion 41, horn member 25 and probe 32. Specifically, a probe-side electricity supply path P1 of high-frequency electric power, which is output from the high-frequency energy source 17, is formed by the electric wiring portion 41, horn member 25 and probe 32. The probe distal portion 33 functions as an electrode, by the high-frequency electric power being supplied (transmitted) to the probe distal portion 33 via the probe-side electricity supply path P1. At this time, in the probe 32, the high-frequency electric power is transmitted from the proximal direction side (probe proximal portion direction side) to the distal direction side (probe distal portion direction side).

As illustrated in FIG. 3, the sheath 31 includes a stationary cylindrical portion 42 which is fixed to the rotary operation knob 8, and a movable cylindrical portion 43 that is an energy transmission portion, which is movable along the longitudinal axis C relative to the stationary cylindrical portion 42. The movable cylindrical portion 43 is located on an inner peripheral side of the stationary cylindrical portion 42, and is formed of an electrically conductive material. A coating (not shown) by an electrically insulative material may be applied to an outer peripheral surface of the stationary cylindrical portion 42 and an inner peripheral surface of the movable cylindrical portion 43. In the present embodiment, the stationary cylindrical portion 42 and movable cylindrical portion 43 extend coaxially with the longitudinal axis C.

The movable cylindrical portion 43 includes a distal end (transmission portion distal end) and a proximal end (transmission portion proximal end). A cavity portion 45 is formed along the longitudinal axis C in the inside of the movable cylindrical portion 43, and the probe 32 extends through the cavity portion 45. The probe distal portion (treatment section) 33 projects from the distal end of the movable cylindrical portion 43 toward the distal direction. Here, a direction toward the distal end (transmission portion distal end) in the movable cylindrical portion (energy transmission portion) 43 is a transmission portion distal direction (sheath distal direction), and a direction toward the proximal end (transmission portion proximal end) in the movable cylindrical portion 43 is a transmission portion proximal direction (sheath proximal direction). In the present embodiment, the transmission portion distal direction agrees with the above-described probe distal portion direction and distal direction, and the transmission portion proximal direction agrees with the above-described probe proximal portion direction and proximal direction.

As illustrated in FIG. 2, a proximal portion (a part on a transmission portion proximal direction side) of the movable cylindrical portion 43 is coupled to the transducer case 12 in the inside of the cylindrical case portion 5. The movable cylindrical portion 43 is movable along the longitudinal axis C relative to the transducer case 12. In addition, the transducer case 12 is provided with an electrically conductive portion 46. In the state in which the movable cylindrical portion 43 is coupled to the transducer case 12, an outer peripheral surface of the proximal portion of the movable cylindrical portion 43 is in contact with the electrically conductive portion 46 of the transducer case 12. Thus, in the state in which the movable cylindrical portion 43 is coupled to the transducer case 12, the movable cylindrical portion 43 and the electrically conductive portion 46 of the transducer case 12 are electrically connected. One end of an electric wiring portion 47 is connected to the electrically conductive portion 46 of the transducer case 12. The other end of the electric wiring portion 47 is electrically connected to the high-frequency energy source 17 of the energy source unit 15. The electric wiring portion 47 extends through the inside of the transducer case 12 and the inside of the cable 13.

As illustrated in FIG. 3, the jaw 35 is attached to a distal portion of the stationary cylindrical portion 42 via a fulcrum pin 51. In addition, a distal portion (a portion on a transmission portion distal direction side) of the movable cylindrical portion 43 is connected to the jaw 35 via a connection pin 52. By opening or closing the movable handle 7 relative to the stationary handle 6, the movable cylindrical portion 43 moves along the longitudinal axis C relative to the stationary cylindrical portion 42 and probe 32. By the movement of the movable cylindrical portion 43 along the longitudinal axis C, the jaw 35 rotates about the fulcrum pin 51 relative to the sheath 31, and the jaw 35 opens or closes relative to the probe distal portion 33.

In addition, in the energy treatment instrument 2, the high-frequency electric power, which was output from the high-frequency energy source 17, can be supplied to the jaw 35 in addition to the probe distal portion 33. The high-frequency electric power, which was output from the high-frequency energy source 17, is supplied to the jaw 35 through the electric wiring portion 47, the electrically conductive portion 46 of the transducer case 12, and the movable cylindrical portion 43 of the sheath 31.

Specifically, a jaw-side electricity supply path P2 of high-frequency electric power, which is output from the high-frequency energy source 17, is formed by the electric wiring portion 47, the electrically conductive portion 46 of the transducer case 12, and the movable cylindrical portion 43 of the sheath 31.

In the meantime, the contact of the probe 32 with the sheath 31, and the contact of the horn member 25 with the transducer case 12 are prevented. Accordingly, short-circuit between the probe-side electricity supply path P1 and jaw-side electricity supply path P2 is prevented. Moreover, transmission of ultrasonic vibration from the vibrating body unit 20 including the probe 32 and horn member 25 to the sheath 31 and transducer case 12 is also prevented, and the sheath 31 and transducer case 12 do not vibrate by ultrasonic vibration.

FIG. 4 is a cross-sectional view taken along line IV-IV in FIG. 3, and FIG. 5 is a cross-sectional view taken along line V-V in FIG. 3. As illustrated in FIG. 3 to FIG. 5, the jaw 35 includes a jaw support portion 53 which is attached to the distal portion of the stationary cylindrical portion 42 and to the distal portion (the portion on the transmission portion distal direction side) of the movable cylindrical portion 43. The jaw support portion 53 is formed of an electrically conductive material, and a coating (not shown) by an electrically insulative material is applied to an exposed surface, which is exposed to the outside of the jaw 35. In addition, in the jaw 35, a jaw swing portion 56 is attached to the jaw support portion 53 via a connection pin 55. The jaw swing portion 56 is swingable about the connection pin 55 relative to the jaw support portion 53. Here, a direction in which the jaw 35 moves toward the probe distal portion (treatment section) 33 is defined as a jaw closing direction (a direction of arrow Y1 in FIG. 3 to FIG. 5), and a direction in which the jaw 35 moves away from the probe distal portion 33 is defined as a jaw opening direction (a direction of arrow Y2 in FIG. 3 to FIG. 5). The jaw opening direction is one of directions crossing the longitudinal axis C, and the jaw closing direction is a direction opposite to the jaw opening direction. The jaw swing portion 56 is attached to a jaw closing direction side of the jaw support portion 53.

The jaw pivot portion 56 includes an electrode member 57 which is formed of an electrically conductive material, and a pad member 58 which is formed of an electrically insulative material. In the present embodiment, the electrode member 57 is attached to the jaw support portion 53 via the connection pin 55, and the pad member 58 is fixed to the electrode member 57. High-frequency electric power, which has been transmitted to the jaw 35 through the jaw-side electricity supply path P2, is transmitted to the electrode member 57 through the jaw support portion 53. The electrode member 57 of the jaw 35 functions as an electrode having an electric potential different from an electric potential of the probe distal portion 33, by the high-frequency electric power being supplied (transmitted) to the electrode member 57 of the jaw 35 as energy which is used for a treatment.

The pad member 58 includes an abutment surface 61 which is abuttable on the probe distal portion 33 in a state in which the jaw 35 closes relative to the probe distal portion 33. The abutment surface 61 is opposed to the probe distal portion 33, and faces toward the jaw closing direction side. In addition, the electrode member 57 includes electrode counter-surfaces 62A and 62B which are opposed to the probe distal portion 33, and face toward the jaw closing direction side. In the state in which the abutment surface 61 of the pad member 58 abuts on the probe distal portion 33, there is a gap between the electrode counter-surfaces 62A and 62B and the probe distal portion 33. Thus, even in the state in which the abutment surface 61 of the pad member 58 abuts on the probe distal portion 33, the electrode member 57 of the jaw 35 does not come in contact with the probe distal portion 33.

A jaw cavity 63 is formed between the jaw support portion 53 and the electrode member 57 of the jaw swing portion 56 in the jaw opening direction and jaw closing direction. Specifically, the jaw cavity 63 is formed in the inside of the jaw 35. The outer surface of the jaw 35 is provided with opening portions 65A and 65B through which the jaw cavity 63 is open to the outside of the jaw 35. The opening portion 65A is open toward one of width directions of the jaw 35, and the opening portion 65B is open toward the other of the width directions of the jaw 35. The opening portions 65A and 65B are located between the jaw support portion 53 and jaw swing portion 56.

In addition, hole-shaped portions 66A and 66B, which penetrate the electrode member 57 from the jaw cavity 63 toward the jaw closing direction side, are formed in the electrode member 57 of the jaw 35. The hole-shaped portion 66A is open to the outside of the jaw 35 on the electrode counter-surface 62A toward the jaw closing direction side, and the hole-shaped portion 66B is open to the outside of the jaw 35 on the electrode counter-surface 62B toward the jaw closing direction side. In the present embodiment, the jaw cavity 63 is located on the jaw opening direction side with respect to the abutment surface 61 of the jaw 35, and is located on the distal direction side with respect to a proximal end E1 of the abutment surface 61. In addition, in this embodiment, the opening portions 65A and 65B and hole-shaped portions 66A and 66B are also located on the jaw opening direction side with respect to the abutment surface 61 of the jaw 35, and are located on the distal direction side with respect to the proximal end E1 of the abutment surface 61. A projection wall 67, which projects toward the jaw opening direction, is formed on the electrode member 57. The projection wall 67 is located on the proximal direction side of the jaw cavity 63, and a proximal end of the jaw cavity 63 is formed by a distal surface 68 of the projection wall 67.

As illustrated in FIG. 2 and FIG. 3, in the present embodiment, a suction conduit 71 may be formed by the hollow portion 37 in the inside of the probe 32 and the cavity portion 28 in the inside of the horn member 25. In this case, one end of a suction tube portion 72 is connected to the horn member 25, and the inside of the suction tube portion 72 communicates with the suction conduit 71. As illustrated in FIG. 1, the other end of the suction tube portion 72 is connected to a suction source 73. The suction source 73 includes a suction actuation section 75 such as a suction pump, and a collection tank 76. The suction actuation section 75 is electrically connected to the controller 18 of the energy source unit 15, and the actuation state of the suction actuation section 75 is controlled by the controller 18.

By the suction actuation section 75 being actuated, a flow (suction force) toward the suction source 73 occurs in the inside of the suction tube portion 72 and suction conduit 71. Specifically, by the suction actuation section 75 being actuated, a flow toward the proximal direction (probe proximal portion direction) occurs in the suction conduit 71. By the flow toward the proximal direction occurring in the suction conduit 71, object to be sucked, which exists on the outside of the probe 32, is sucked into the suction conduit 71 through the opening portion 38. Then, the sucked object is collected into the collection tank 76 through the suction conduit 71 and the inside of the suction tube portion 72. In the meantime, in a certain embodiment, a tube member (not shown) may extend from the proximal direction side to the distal direction side in the hollow portion 37 in the inside of the probe 32, and a suction conduit (71) may be formed in the inside of the tube member.

Figure 6:
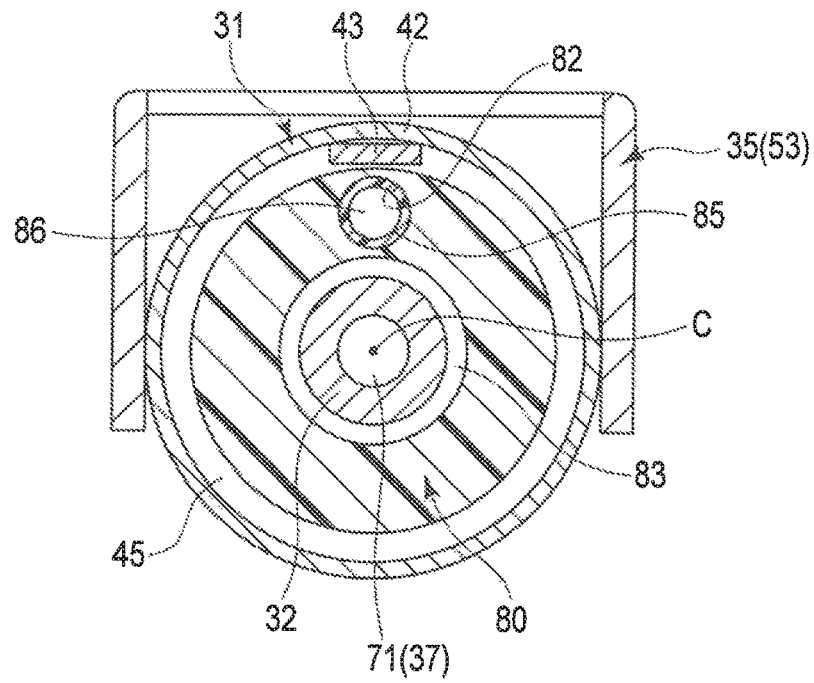
FIG. 6 is a cross-sectional view taken along line VI-VI in FIG. 3.

FIG. 6 is a cross-sectional view taken along line VI-VI in FIG. 3. As illustrated in FIG. 3 and FIG. 6, a multi-lumen tube 80 extends from the proximal direction side toward the distal direction side in the cavity portion 45 in the inside of the movable cylindrical portion (energy transmission portion) 43 of the sheath 31. In this embodiment, an energy treatment unit 30, which is used together with the probe, is formed by the sheath 31 (movable cylindrical portion 43), jaw 35 and multi-lumen tube 80. The multi-lumen tube 80 includes a proximal end and a distal end. In this embodiment, the proximal end of the multi-lumen tube 80 is located in the inside of the cylindrical case portion 5. The position of the distal end of the multi-lumen tube 80 substantially agrees with the position of the distal end of the sheath 31 (the transmission portion distal end of the movable cylindrical portion 43) in the longitudinal direction that is parallel to the longitudinal axis C. The multi-lumen tube 80 includes a tube reference surface 81 which faces toward the distal direction. In this embodiment, the distal end of the multi-lumen tube 80 is formed by the tube reference surface 81.

In the multi-lumen tube 80, a first lumen 82 and a second lumen 83 are formed from the proximal direction side toward the distal direction side. The first lumen 82 and second lumen 83 penetrate the multi-lumen tube 80 in the longitudinal direction. The first lumen 82 and second lumen 83 are isolated from each other. Accordingly, in the multi-lumen tube 80, the first lumen 82 and second lumen 83 do not communicate with each other. The probe 32 is inserted in the second lumen 83. In the present embodiment, distal ends of the first lumen 82 and second lumen 83 are located on the tube reference surface 81.

A proximal end of a connection tube 85 is connected to the distal end of the first lumen 82 of the multi-lumen tube 80. The inside of the connection tube 85 communicates with the first lumen 82. A distal end of the connection tube 85 is connected to the jaw 35 in the projection wall 67 of the electrode member 57. The inside of the connection tube 85 communicates with the jaw cavity 63. In this embodiment, a liquid feed conduit 86 is formed through the first lumen 82 and the inside of the connection tube 85. In addition, an ejection port 87 of the liquid feed conduit 86 is formed at the distal end of the connection tube 85. Specifically, the liquid feed conduit 86 extends from the proximal direction side toward the distal direction side, through between the movable cylindrical portion (energy transmission portion) 43 and probe 32, and the ejection port 87 is formed at the distal end of the liquid feed conduit 86 which is located at the distal end of the connection tube 85. In this embodiment, the ejection port 87 is located on the distal direction side with respect to the proximal end E1 of the abutment surface 61. In addition, the jet port 87 is located on the distal direction side with respect to the tube reference surface 81 which is located at the distal end of the sheath 31. Specifically, the ejection port 87 is located on the distal direction side with respect to the proximal end of the probe distal portion (treatment section) 33. The connection tube 85 is formed of, for example, a material with flexibility, and the connection tube 85 can flex in accordance with the opening and closing of the jaw 35.

In addition, one end of a liquid feed tube portion 91 is connected to a proximal end of the first lumen 82 of the multi-lumen tube 80, and the inside of the liquid feed tube portion 91 communicates with the liquid feed conduit 86 (first lumen 82). In the inside of the cylindrical case portion 5, the liquid feed tube portion 91 extends from the cavity portion 45 in the inside of the sheath 31 to the outside of the sheath 31. Furthermore, the liquid feed tube portion 91 extends through the inside of the cylindrical case portion 5 and the inside of the stationary handle 6. In this embodiment, the liquid feed tube portion 91 extends to the outside of the holding unit 3 at the stationary handle 6.

As illustrated in FIG. 1, the other end of the liquid feed tube portion 91 is connected to a liquid feed source 92. The liquid feed source 92 includes a liquid feed actuation section 93 such as a liquid feed pump, and a liquid storage tank 95. The liquid feed actuation section 93 is electrically connected to the controller 18 of the energy source unit 15, and the actuation state of the liquid feed actuation section 93 is controlled by the controller 18. By the liquid feed actuation section 93 being actuated, a liquid, such as physiological saline, which is stored in the liquid storage tank 95, is supplied (fed) to the liquid feed conduit 86 through the inside of the liquid feed tube portion 91. In addition, in the liquid feed conduit 86, the liquid is supplied from the proximal direction (transmission portion proximal direction) to the distal direction (transmission portion distal direction).

In addition, the liquid, which is supplied through the liquid feed conduit 86, is ejected toward the distal direction side from the ejection port 87 which is located at the distal end of the connection tube 85. Since the liquid feed conduit 86 and the jaw cavity 63 communicate with each other, the liquid ejected from the ejection port 87 flows into the jaw cavity 63. Then, the liquid flows from the jaw cavity 63 to the outside of the jaw 35 through the opening portions 65A and 65B and hole-shaped portions 66A and 66B. Specifically, the opening portions 65A and 65B and hole-shaped portions 66A and 66B function as a liquid outflow portion from which the liquid flowing in the jaw cavity 63 flows to the outside of the jaw 35. Here, the opening portions 65A and 65B and hole-shaped portions 66A and 66B are located on the jaw opening direction side with respect to the abutment surface 61 of the jaw 35, and are located on the distal direction side with respect to the proximal end E1 of the abutment surface 61. Thus, the liquid flows to the outside of the jaw 35 from a position located on the jaw opening direction side with respect to the abutment surface 61 of the jaw 35 and located on the distal direction side with respect to the proximal end E1 of the abutment surface 61.

Additionally, the projection wall 67 is formed on the proximal direction side of the jaw cavity 63. Thus, by the liquid colliding with the distal surface 68 of the projection wall 67 in the jaw cavity 63, the outflow of the liquid from the jaw cavity 63 to the proximal direction side is prevented. Since the outflow of the liquid from the jaw cavity 63 to the proximal direction side is prevented by the projection wall 67 that is a collision wall, the outflow of the liquid to the outside of the jaw 35 from a region located on the proximal direction side with respect to the proximal end E1 of the abutment surface 61 can effectively be prevented.

Next, the functions and advantageous effects of the energy treatment unit 30 and energy treatment instrument 2 of the present embodiment will be described. When a treated target, such as a biological tissue, is treated by the energy treatment system 1, the probe distal portion (treatment section) 33 and jaw 35 are inserted into the body. Then, for example, in a certain treatment, the treated target is disposed between the probe distal portion 33 and jaw 35, and the movable handle 7 is closed relative to the stationary handle 6. In accordance with the closing movement of the movable handle 7, the movable cylindrical portion 43 moves along the longitudinal axis C. Thereby, the jaw 35 closes relative to the probe distal portion 33, and the treated target is grasped between the probe distal portion (treatment section) 33 and jaw 35.

In the present embodiment, the connection tube 85 (liquid feed conduit 86) projects toward the distal direction side from the distal end of the movable cylindrical portion 43 (the distal end of the sheath 31). However, the distal end of the connection tube 85 is connected to the electrode member 57 of the jaw 35. Thus, the projecting portion of the connection tube 85, which projects from the distal end of the sheath 31, does not extend on the outer surface of the probe distal portion 33, but is located on the jaw opening direction side with respect to the abutment surface 61 of the jaw 35. Therefore, when the treated target is grasped between the jaw 35 and probe distal portion 33, the treated target does not interfere with the connection tube 85 (liquid feed conduit 86). Since the treated target is prevented from interfering with the liquid feed conduit 86, the grasping performance can be secured when the treated target is grasped between the jaw 35 and probe distal portion 33.

In the state in which the treated target is grasped between the jaw 35 and probe distal portion 33, an energy operation is input by the energy operation input button 9A. By the input of the energy operation by the energy operation input button 9A, ultrasonic electric power is supplied to the ultrasonic transducer 21 from the ultrasonic energy source 16, and ultrasonic vibration is generated by the ultrasonic transducer 21. Then, the generated ultrasonic vibration is transmitted to the probe distal portion (treatment section) 33 via the probe 32 (vibrating body unit 20). In addition, by the input of the energy operation by the energy operation input button 9A, high-frequency electric power is output from the high-frequency energy source 17. Then, the high-frequency electric power is supplied to the probe distal portion 33 through the probe-side electricity supply path P1, and the high-frequency electric power is supplied to the electrode member 57 of the jaw 35 through the jaw-side electricity supply path P2. Thereby, the probe distal portion 33 and the electrode member 57 of the jaw 35 function as electrodes with mutually different electric potentials. In the state in which the treated target is grasped between the jaw 35 and probe distal portion 33, the probe distal portion 33 longitudinally vibrates, and thereby frictional heat occurs between the probe distal portion 33 and the treated target. By the frictional heat, the treated target is coagulated and, at the same time, cut. In addition, in the state in which the treated target is grasped between the jaw 35 and probe distal portion 33, the probe distal portion (treatment section) 33 and the electrode member 57 of the jaw 35 function as the electrodes. Thereby, a high-frequency current flows between the probe distal portion 33 and the electrode member 57 via the treated target. Thereby, the treated target is denatured, and coagulation is promoted.

Additionally, in another treatment, an energy operation is input by the energy operation input button 9B. Thereby, high-frequency electric power is supplied to the probe distal portion 33 through the probe-side electricity supply path P1, and the high-frequency electric power is supplied to the electrode member 57 of the jaw 35 through the jaw-side electricity supply path P2. Thereby, the probe distal portion 33 and the electrode member 57 function as electrodes with mutually different electric potentials. At this time, no ultrasonic electric power is output from the ultrasonic energy source 16, nor does ultrasonic vibration generate. In addition, by the input of the energy operation by the energy operation input button 9B, the liquid feed actuation unit 93 is actuated, and a liquid, such as physiological saline, is supplied toward the distal direction side in the liquid feed conduit 86. In addition, the liquid ejected from the ejection port 87 flows into the jaw cavity 63, and the liquid flowing in the jaw cavity 63 flows to the outside of the jaw 35 from the liquid outflow portion (opening portions 65A and 65B and hole-shaped portions 66A and 66B). Thereby, the liquid is supplied to the grasped treated target. By the liquid being supplied to the treated target which is grasped in the state in which the probe distal portion 33 and electrode member 57 function as electrodes, a bipolar treatment is performed in which a high-frequency current is caused to flow in the treated target via the liquid between the probe distal portion 33 and the electrode member 57 of the jaw 35.

Here, in the state in which the treated target is grasped between the probe distal portion 33 and the jaw 35, the abutment surface 61 comes in contact with the treated target, and that part of the jaw 35, which is located on the proximal direction side with respect to the proximal end E1 of the abutment surface 61, is not put in contact with the treated target. It is thus necessary to make the liquid, which is used for the treatment, reach the region located on the distal direction side with respect to the proximal end E1 of the abutment surface 61. In the present embodiment, the liquid outflow portion (opening portions 65A and 65B and hole-shaped portions 66A and 66B) is located on the distal direction side with respect to the proximal end E1 of the abutment surface 61. Thus, the liquid flows to the outside of the jaw 35 from a position located on the distal direction side with respect to the proximal end E1 of the abutment surface 61. Accordingly, in this embodiment, the liquid, which is used for the treatment, surely reaches the region located on the distal direction side with respect to the proximal end E1 of the abutment surface 61, and the liquid flowing out of the jaw cavity 63 is properly supplied to the treated target which is in contact with the abutment surface 61. Thereby, the performance in supplying liquid to the treated target can be secured.

Additionally, in this embodiment, the jet port 87 of the liquid feed conduit 86 is located on the distal direction side with respect to the proximal end E1 of the abutment surface 61 of the jaw 35. Thus, the liquid flows in the jaw cavity 63 from a position located on the distal direction side with respect to the proximal end E1 of the abutment surface 61 of the jaw 35. Thereby, the liquid surely flows to the outside of the jaw 35 from a position located on the distal direction side with respect to the proximal end E1 of the abutment surface 61, and the performance in supplying liquid to the treated target is improved.

Additionally, in the jaw cavity 63, since the liquid collides with the distal surface 68 of the projection wall (collision wall) 67, the outflow of liquid from the jaw cavity 63 to the proximal direction side is prevented. Thereby, the outflow of the liquid to the outside of the jaw 35 from the region located on the proximal direction side with respect to the proximal end E1 of the abutment surface 61 can effectively be prevented. Therefore, the performance in supplying liquid to the treated target is improved.

Additionally, since the outflow of the liquid to the outside of the jaw 35 from the region located on the proximal direction side with respect to the proximal end E1 of the abutment surface 61 is prevented, discharge of high-frequency current (high-frequency electric power) via the liquid from the jaw 35 on the region located on the proximal direction side with respect to the proximal end E1 of the abutment surface 61 is effectively prevented. Thereby, the treatment performance in treatment can be secured.

Additionally, in another treatment, an energy operation is input by the energy operation input switch 10. Thereby, ultrasonic electric power is supplied to the ultrasonic transducer 21 from the ultrasonic energy source 16, and ultrasonic vibration is generated by the ultrasonic transducer 21. Then, the caused ultrasonic vibration is transmitted to the probe distal portion 33 via the probe 32 (vibrating body unit 20). In addition, by the input of the energy operation by the energy operation input switch 10, the liquid feed actuation section 93 is actuated and the suction actuation section 75 is actuated. Thereby, the liquid, which has been supplied through the liquid feed conduit 86, is ejected from the ejection port 87, and the liquid ejected from the ejection port 87 flows into the jaw cavity 63. Then, the liquid flowing into the jaw cavity 63 flows to the outside of the jaw 35 from the liquid outflow portion (opening portions 65A and 65B and hole-shaped portions 66A and 66B).

In the state in which the probe distal portion 33 (probe 32) longitudinally vibrates at high speed, the liquid is supplied to the vicinity of the distal surface of the probe distal portion 33. Thereby, cavitation occurs near the distal surface of the probe distal portion 33. By the cavitation occurring in the state in which the treated target is located near the distal surface of the probe distal portion 33, the treated target is crushed and emulsified. In the meantime, in the cavitation, only a biological tissue with low resiliency, such as hepatic cells, is selectively crushed, and a biological tissue with resiliency, such as a blood vessel, is not shattered. In addition, the crushed and emulsified treated target is sucked into the suction conduit 71 through the opening portion 38 on the outer surface of the probe distal portion 33. Further, the sucked object, which was sucked in the suction conduit 71, moves toward the proximal direction side.

As described above, in the present embodiment, the liquid flows to the outside of the jaw 35 from the position located on the distal direction side with respect to the proximal end E1 of the abutment surface 61. Accordingly, in this embodiment, the liquid, which is used for the treatment, surely reaches the region located on the distal direction side of the proximal end E1 of the abutment surface 61, and the liquid flowing out of the jaw cavity 63 is properly supplied to the treated target in the vicinity of the distal surface of the probe distal portion 33. Thereby, the cavitation properly occurs, and the treated target can be properly crushed and emulsified.

Additionally, since the liquid is supplied as described above, the liquid does not come in contact with the probe 32 (vibrating body unit 20) along the path of the liquid from the jaw cavity 63 to the outflow to the outside of the jaw 35, and the liquid does not pass through the outer surface of the probe 32 (probe distal portion 33). Since the liquid does not come in direct contact with the outer surface of the probe 32 (treatment section), the load acting on the probe 32 does not increase in the state in which the probe 32 vibrates by ultrasonic vibration, and the ultrasonic impedance does not increase. Thus, in order to secure the amplitude of longitudinal vibration in the probe distal portion 33, there is no need to increase the ultrasonic electric power (energy), which is supplied to the ultrasonic transducer (vibration generating section) 21, in accordance with the load. Specifically, the ultrasonic electric power (voltage), which is supplied to the ultrasonic transducer 21, can be suppressed to be low. Thereby, the energy efficiency at a time of causing the probe 32 to vibrate by ultrasonic vibration can be secured.

Additionally, the liquid outflow portion (opening portions 65A and 65B and hole-shaped portions 66A and 66B) is located on the jaw opening direction side with respect to the abutment surface 61 of the jaw 35. Thus, the liquid flows to the outside of the jaw 35 from the position located on the jaw opening direction side with respect to the abutment surface 61 of the jaw 35. Since the liquid flows out from the position located on the jaw opening direction side with respect to the abutment surface 61 of the jaw 35, the liquid flowing out of the jaw cavity 63 hardly adheres to the outer surface of the probe distal portion 33. Since the liquid hardly adheres to the outer surface of the probe distal portion 33, the load acting on the probe 32 decreases in the state in which the probe 32 vibrates by ultrasonic vibration, and the ultrasonic electric power (voltage), which is supplied to the ultrasonic transducer 21, can be suppressed to be still lower.

As has been described above, according to the present embodiment, there can be provided the energy treatment unit 30 and energy treatment 2, which secure the performance in grasping a treated target between the jaw 35 and probe distal portion 33, and the performance in supplying liquid to the treated target, and secure the energy efficiency in a treatment in which energy is used.

(Modifications)

Figure 7:
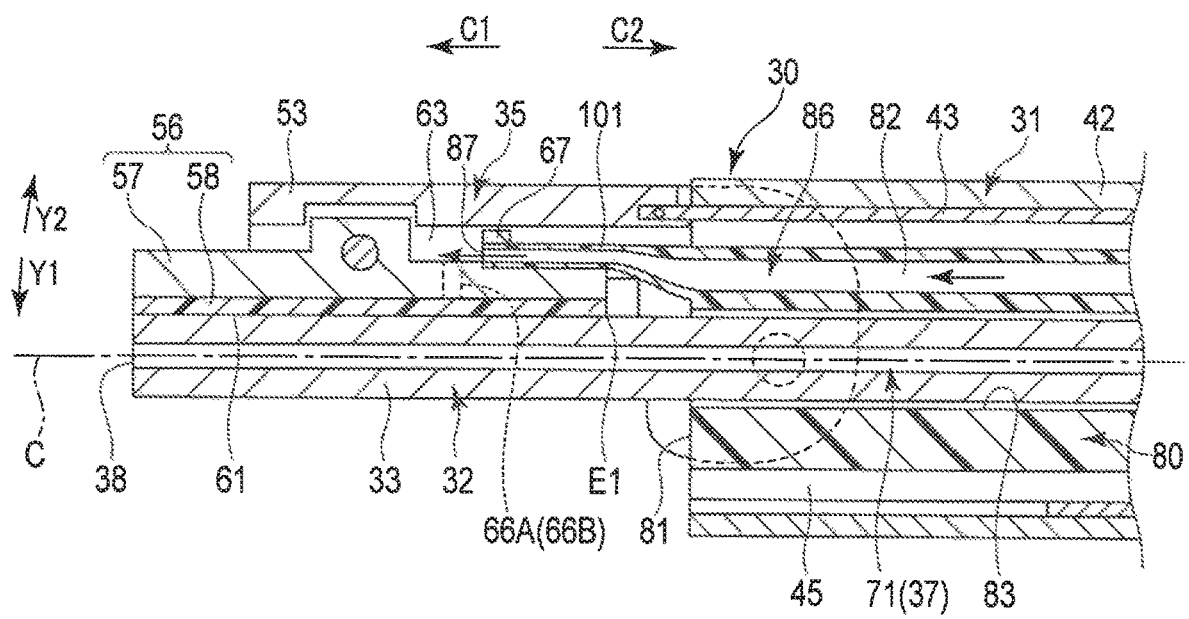
FIG. 7 is a cross-sectional view which schematically illustrates the configuration of a distal portion of an energy treatment instrument including a probe distal portion and a jaw according to a first modification.

In the meantime, in the first embodiment, the multi-lumen tube 80 and jaw 35 are coupled via the connection tube 85, but the restriction to this is unnecessary. For example, as illustrated in FIG. 7 as a first modification, the connection tube 85 may not be provided. In the present modification, a tube projection portion 101, which projects from the tube reference surface 81 toward the distal direction side, is provided in the multi-lumen tube 80. Thus, the tube reference surface 81 functions as a tube base surface which is a base surface of the tube projection portion 101. The tube projection portion 101 is formed as one piece with the multi-lumen tube 80.

In the present modification, the first lumen 82 extends through the inside of the tube projection portion 101. Accordingly, only the distal end of the second lumen 83 is located on the tube reference surface (tube base surface) 81, and the distal end of the first lumen 82 is located on the distal direction side with respect to the tube reference surface 81.

In the present modification, a distal end of the tube projection portion 101 of the multi-lumen tube 80 is connected to the electrode member 57 of the jaw 35. In addition, the ejection port 87 of the liquid feed conduit 86 is formed at the distal end of the tube projection portion 101. Accordingly, in this modification, the jet port 87 is located at the distal end of the first lumen 82.

In this modification, like the first embodiment, the liquid ejected from the ejection port 87 flows into the jaw cavity 63. Then, the liquid flowing in the jaw cavity 63 flows to the outside of the jaw 35 from the liquid outflow portion (opening portions 65A and 65B and hole-shaped portions 66A and 66B). Accordingly, in this modification, too, the liquid flows to the outside of the jaw 35 from a position located on the jaw opening direction side with respect to the abutment surface 61 of the jaw 35 and located on the distal direction side with respect to the proximal end E1 of the abutment surface 61.

Figure 8:
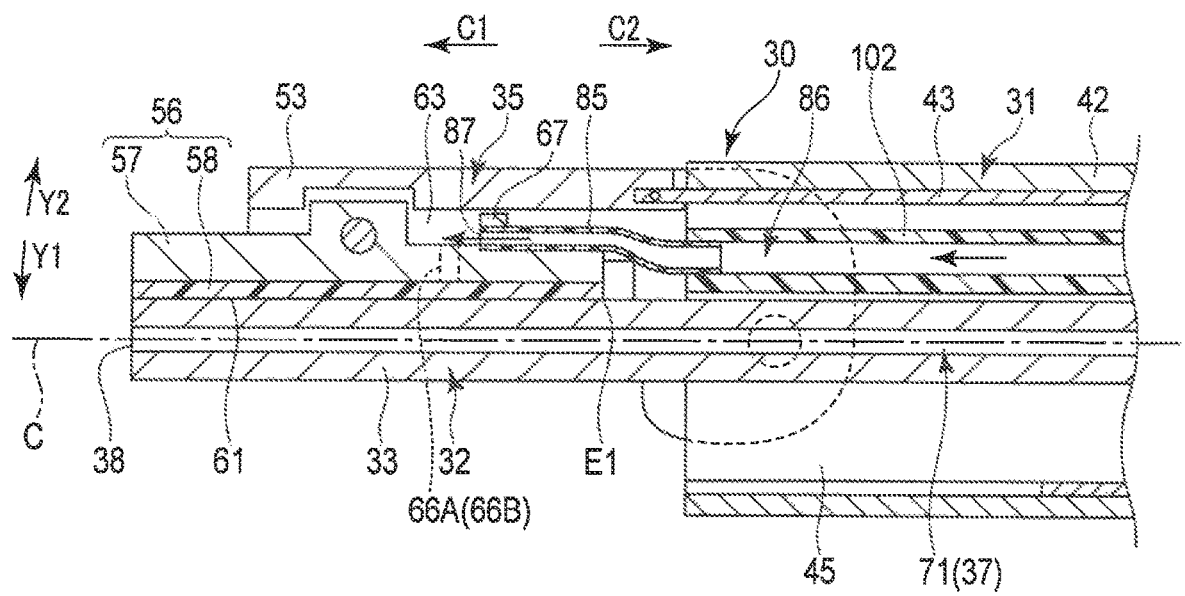
FIG. 8 is a cross-sectional view which schematically illustrates the configuration of a distal portion of an energy treatment instrument including a probe distal portion and a jaw according to a second modification.

Additionally, as illustrated in FIG. 8 as a second modification, the multi-lumen tube 80 may not be provided. In the present modification, a tube member 102 is provided in place of the multi-lumen tube 80. In this modification, an energy treatment unit 30, which is used together with the probe, is formed by the sheath 31 (movable cylindrical portion 43), jaw 35 and tube member 102. The tube member 102 extends from the proximal direction side to the distal direction side in the cavity portion 45 between the movable cylindrical member 43 and probe 32. The position of a distal end of the tube member 102 substantially agrees with the position of the distal end of the sheath 31 in the longitudinal direction.

In this modification, a proximal end of the connection tube 85 is connected to the distal end of the tube member 102. Like the first embodiment, the distal end of the connection tube 85 is connected to the electrode member 57 of the jaw 35. In this modification, the liquid feed conduit 86 is formed in the inside of the tube member 102 and the inside of the connection tube 85. Besides, the ejection port 87 is formed at the distal end of the connection tube 85.

In this modification, like the first embodiment, the liquid ejected from the ejection port 87 flows into the jaw cavity 63. Then, the liquid flowing in the jaw cavity 63 flows to the outside of the jaw 35 from the liquid outflow portion (opening portions 65A and 65B and hole-shaped portions 66A and 66B). Accordingly, in this modification, too, the liquid flows to the outside of the jaw 35 from a position located on the jaw opening direction side with respect to the abutment surface 61 of the jaw 35 and located on the distal direction side with respect to the proximal end E1 of the abutment surface 61. Furthermore, since the liquid feed conduit 86 passes through the inside of the tube member 102, the liquid does not come in direct contact with the outer surface of the probe 32 (treatment section) along the path up to where the liquid flows to the outside of the jaw 35.

Figure 9:
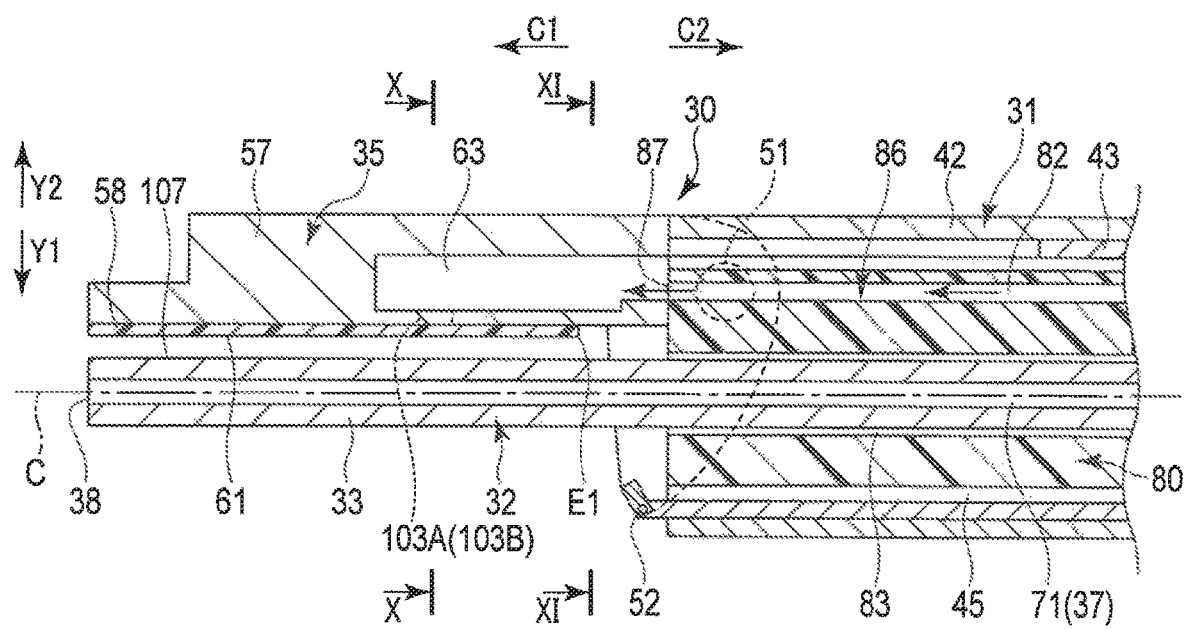
FIG. 9 is a cross-sectional view which schematically illustrates the configuration of a distal portion of an energy treatment instrument including a probe distal portion and a jaw according to a third modification.
Figure 10:
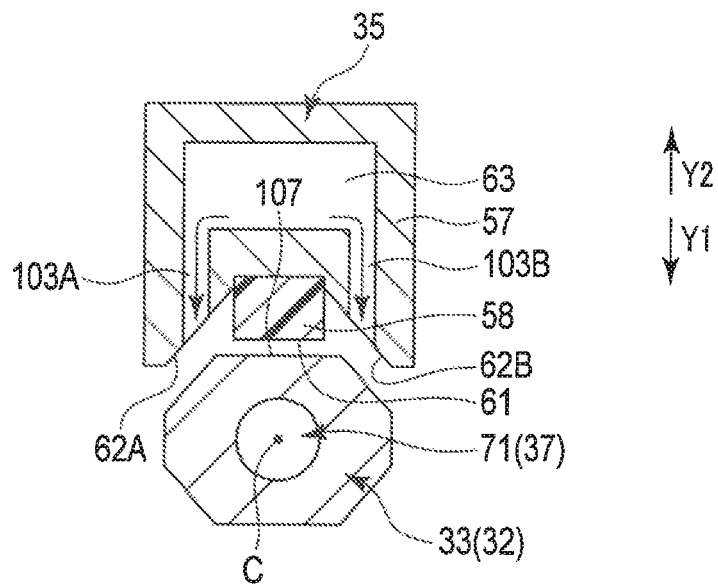
FIG. 10 is a cross-sectional view taken along line X-X in FIG. 9.
Figure 11:
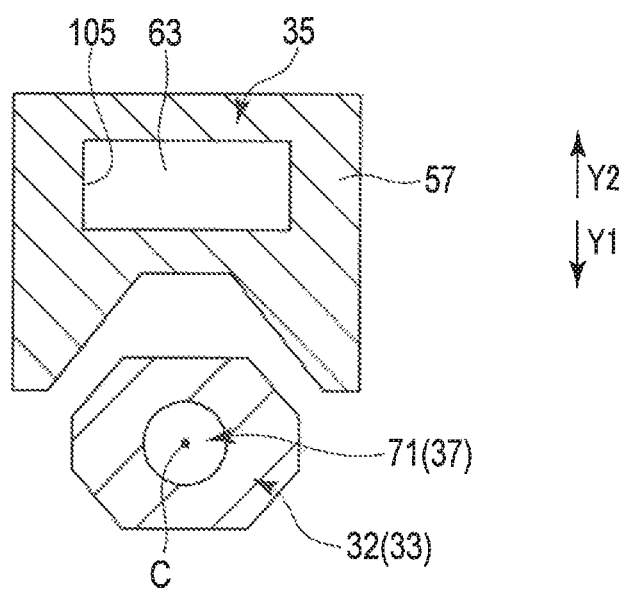
FIG. 11 is a cross-sectional view taken along line XI-XI in FIG. 9.

Additionally, in a third modification illustrated in FIG. 9 to FIG. 11, the ejection port 87 of the liquid feed conduit 86 is located on the proximal direction side with respect to the proximal end E1 of the abutment surface 61. Here, FIG. 9 is a view illustrating a distal portion of the energy treatment instrument 2 including the jaw 35 and probe distal portion 33. FIG. 9 illustrates a state in which the abutment surface 61 of the jaw 35 does not abut on the probe distal portion 33, and there is a gap between the abutment surface 61 and the probe distal portion 33. FIG. 10 is a cross-sectional view taken along line X-X in FIG. 9, and FIG. 11 is a cross-sectional view taken along line XI-XI in FIG. 9.

In this modification, the jaw 35 is formed of only an electrode member 57 and a pad member 58. Thus, the electrode member 57 is attached to the sheath (stationary cylindrical portion 42 and movable cylindrical portion 43) via a fulcrum pin 51 and a connection pin 52. In addition, a jaw cavity 63 is formed in the inside of the electrode member 57. In this modification, too, the pad member 58 is fixed to the electrode member 57, and the abutment surface 61 is provided on the pad member 58. A proximal end of the jaw cavity 63 is open to the outside of the jaw 35, and is located on the proximal direction side with respect to the proximal end E1 of the abutment surface 61.

In a treatment, the jaw 35 is closed relative to the probe distal portion 33 from a state in which the jaw 35 opens relative to the probe distal portion 33 to a maximum degree to a state illustrated, for example, in FIG. 9, and a treated target is grasped between the jaw 35 and probe distal portion 33. At this time, the treated target is located in the gap between the abutment surface 61 of the jaw 35 and the probe distal portion 33. The probe distal portion 33 is provided with a receiving surface 107 on which the abutment surface 61 of the jaw 35 can abut. In the state of FIG. 9, the abutment surface 61 of the jaw 35 is substantially parallel to the receiving surface 107.

In the state of FIG. 9 (i.e. the state in which the treated target is grasped between the jaw 35 and probe distal portion 33), the electrode member 57 is in contact with the tube reference surface (distal surface) 81 of the multi-lumen tube 80, and the ejection port 87 of the liquid feed conduit 86 communicates directly with the proximal end of the jaw cavity 63 at the tube reference surface 81. By the ejection port 87 communicating with the jaw cavity 63, the liquid ejected from the ejection port 87 flows into the jaw cavity 63. At this time, since the jet port 87 communicates with the proximal end of the jaw cavity 63 at a position located on the proximal direction side with respect to the proximal end E1 of the abutment surface 61, the liquid flows from the jet port 87 into the jaw cavity 63 at a position located on the proximal direction side with respect to the proximal end E1 of the abutment surface 61.

As illustrated in FIG. 10, in the present modification, in the electrode member 57, hole-shaped portions 103A and 103B are formed from the jaw cavity 63 to the electrode counter-surfaces 62A and 62B toward the jaw closing direction. The liquid flowing in the jaw cavity 63 flows to the outside of the jaw 35 from the jaw cavity 63 through the hole-shaped portions 103A and 103B. Specifically, the hole-shaped portions 103A and 103B function as a liquid outflow portion from which the liquid flowing in the jaw cavity 63 flows to the outside of the jaw 35. The hole-shaped portions 103A and 103B are located on the jaw opening direction side with respect to the abutment surface 61 of the jaw 35, and are located on the distal direction side with respect to the proximal end E1 of the abutment surface 61. Thus, in the present modification, like the first embodiment, the liquid flows from the jaw cavity 63 to the outside of the jaw 35 from a position located on the jaw opening direction side with respect to the abutment surface 61 of the jaw 35 and located on the distal direction side with respect to the proximal end E1 of the abutment surface 61.

In addition, as illustrated in FIG. 11, in a region located on the proximal direction side with respect to the proximal end E1 of the abutment surface 61, the entire circumference of the jaw cavity 63 is surrounded by a collision wall 105. Thus, by the liquid colliding with the collision wall 105 in the jaw cavity 63, the outflow of the liquid from the jaw cavity 63 is prevented. Specifically, on the region located on the proximal direction side with respect to the proximal end E1 of the abutment surface 61, the outflow of the liquid from the jaw cavity 63 to the jaw opening direction side, to the jaw closing direction side and to the two width direction sides is prevented by the collision wall 105. Thereby, in this modification, like the first embodiment, the outflow of the liquid to the outside of the jaw 35 from the region located on the proximal direction side with respect to the proximal end E1 of the abutment surface 61 can effectively be prevented.

Figure 12:
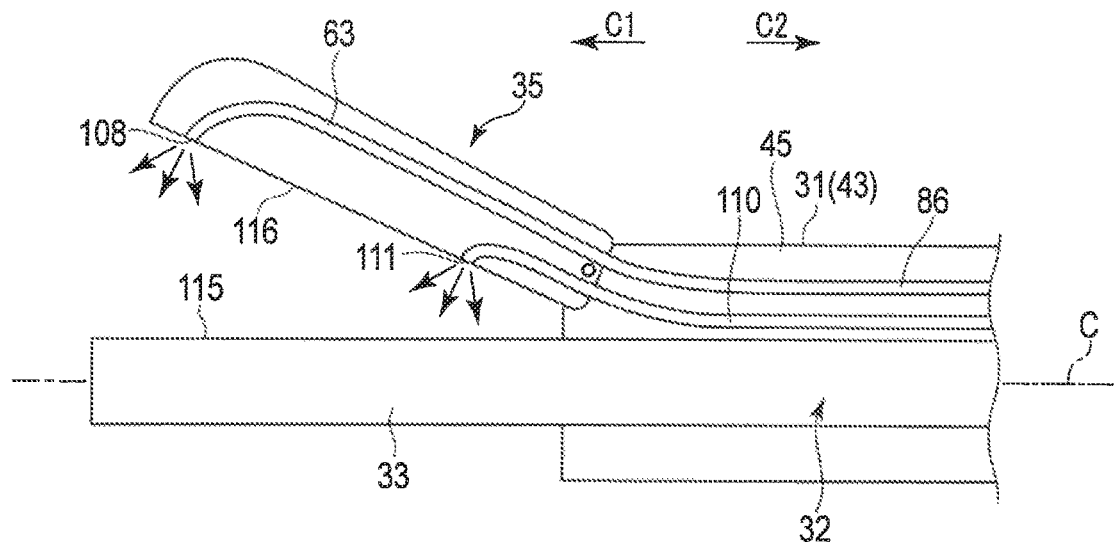
FIG. 12 is a schematic view illustrating the configuration of a distal portion of an energy treatment instrument including a probe distal portion and a jaw according to a fourth modification.

Additionally, in a fourth modification illustrated in FIG. 12, in addition to the liquid feed conduit 86, a gas feed conduit 110 extends from the proximal direction side to the distal direction side in the cavity portion 45 in the inside of the movable cylindrical portion (energy transmission portion) 43 of the sheath 31. In the present modification, too, the liquid flows into the jaw cavity 63 in the inside of the jaw 35 from the liquid feed conduit 86. Then, at a liquid outflow portion 108, the liquid flows to the outside of the jaw 35 from the jaw cavity 63. In the meantime, the liquid outflow portion 108 may have the same configuration (65A, 65B, 66A, 66B) as in the first modification, or may have the same configuration (103A, 103B) as in the third modification. In this modification, the liquid outflow portion 108 is provided in the distal portion of the jaw 35. In this modification, too, the liquid flows to the outside of the jaw 35 from the jaw cavity 63, at the position located on the jaw opening direction side with respect to the abutment surface 61 of the jaw 35 and located on the distal direction side with respect to the proximal end E1 of the abutment surface 61.

The gas feed conduit 110 extends from the inside of the movable cylindrical portion 43 through the inside of the jaw 35. In addition, the gas feed conduit 110 is isolated from the liquid feed conduit 86 and jaw cavity 63. Accordingly, the gas feed conduit 110 does not communicate with the liquid feed conduit 86 and jaw cavity 63, and the liquid, which is fed through the liquid feed conduit 86 and jaw cavity 63, does not flow into the gas feed conduit 110.

The outer surface of the probe distal portion 33 includes a probe counter-surface 115 which is opposed to the jaw 35, and the outer surface of the jaw 35 includes a jaw counter-surface 116 which is opposed to the probe distal portion 33. The abutment surface 61 forms a part of the jaw counter-surface 116. The gas feed conduit 110 includes a gas ejection port 111 which is open to the outside of the jaw 35 on the jaw counter-surface 116. The gas ejection port 111 is located on the proximal direction side with respect to the liquid outflow portion 108 of the jaw cavity 63, and, in this modification, the gas jet port 111 is located in a proximal portion of the jaw 35. A gas is fed from a gas feed source (not shown) through the gas feed conduit 110, and thereby the gas is ejected from the gas ejection port 111 to the outside of the jaw 35. The gas is ejected from the gas ejection port 111 toward the probe counter-surface 115 of the probe 33.

As described above in connection with the first embodiment, there is a case of performing a bipolar treatment in which a high-frequency current is caused to flow in the treated target via the liquid between the probe distal portion 33 and the electrode member 57 of the jaw 35. At this time, depending on the attitude of the energy treatment instrument 2, there is a possibility that the liquid flowing from the liquid outflow portion 108 to the outside of the jaw 35 flows to the proximal direction side via the outer surface of the probe distal portion 33.

Thus, in this modification, the gas ejection port 111 is formed on the proximal direction side with respect to the liquid outflow portion 108 on the outer surface of the jaw 35, and the gas is ejected from the gas ejection port 111 toward the probe distal portion 33, at the same time as the liquid is caused to flow from the liquid outflow portion 108. Thus, even if the liquid flowing out of the liquid outflow portion 108 flows to the proximal direction side, the liquid adhering to the outer surface of the probe distal portion 33 (in particular, the probe counter-surface 115) is removed by the gas ejected from the gas ejection port 111. Thereby, the inflow of liquid into the cavity portion 45 in the inside of the movable cylindrical portion 43 (sheath 31) is prevented, and the flow of high-frequency current between the movable cylindrical portion 43 and probe 32 via the liquid in the cavity portion 45 (i.e. short-circuit) is prevented. Thereby, the treatment performance in the treatment can be secured.

In the meantime, in this modification, the gas feed conduit 110 extends through the cavity portion 45 in the inside of the movable cylindrical portion 43, but the restriction to this is unnecessary. In a certain modification, the gas feed conduit 110 extends via the outside of the sheath 31, and is inserted in the inside of the jaw 35. In this case, too, the gas ejection port 111 is provided at the outer surface of the jaw 35, and gas is ejected to the outside of the jaw from the gas feed conduit 110 at the gas ejection port 111.

Figure 13:
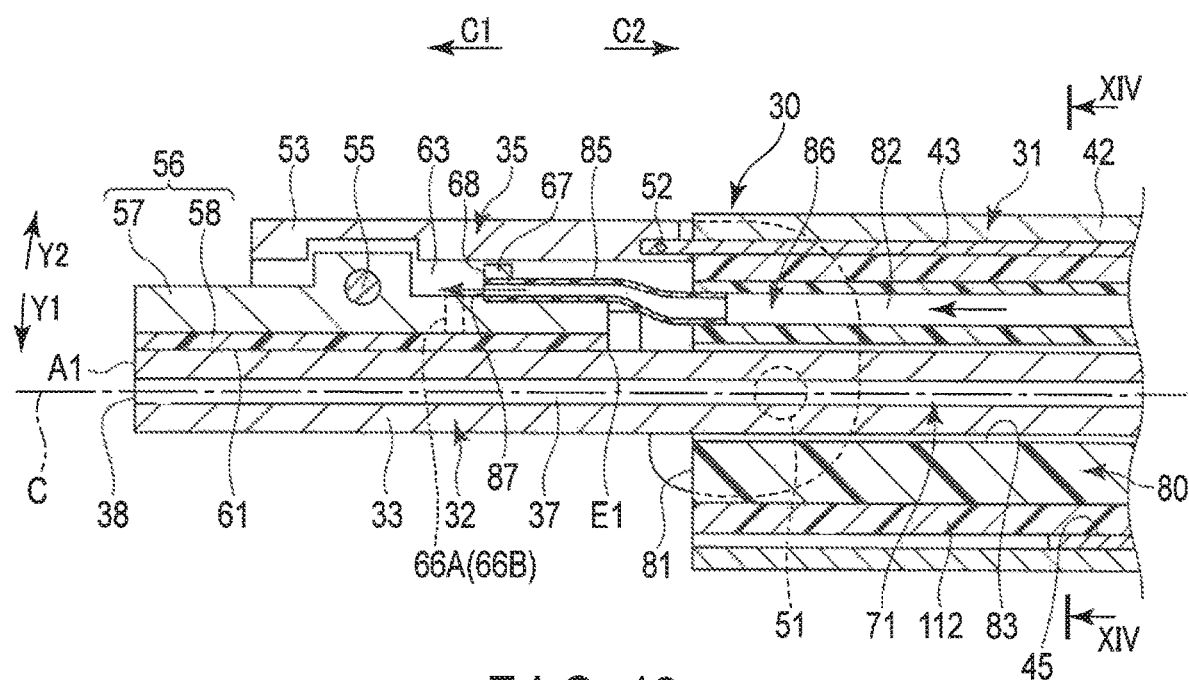
FIG. 13 is a cross-sectional view which schematically illustrates the configuration of a distal portion of an energy treatment instrument including a probe distal portion and a jaw according to a fifth modification.
Figure 14:
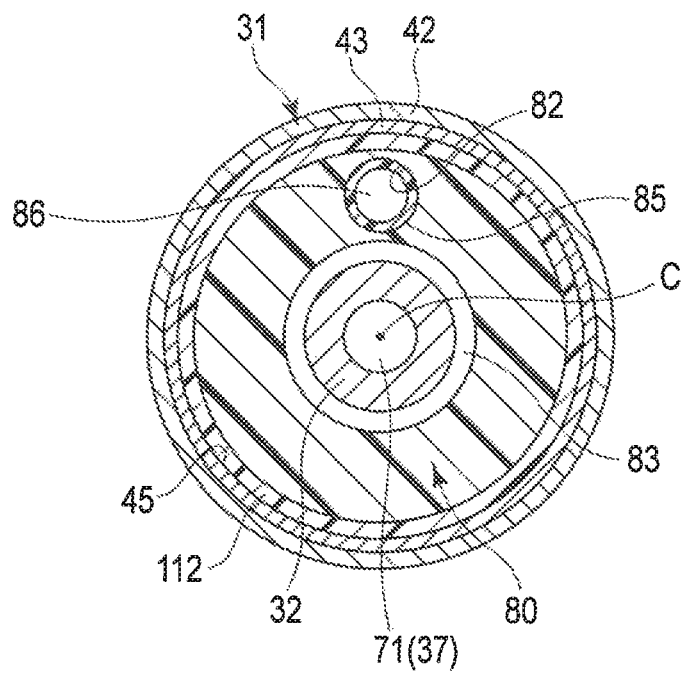
FIG. 14 is a cross-sectional view taken along line XIV-XIV in FIG. 13.

Additionally, in a fifth modification illustrated in FIG. 13 and FIG. 14, a seal member 112 is provided in a distal portion of the cavity portion 45 which is formed in the inside of the movable cylindrical portion (energy transmission portion) 43. Here, FIG. 13 illustrates the configuration of a distal portion (a part on the distal direction side) of an energy treatment instrument 2 including a probe distal portion (treatment section) 33 and a jaw 35 according to a fifth modification. FIG. 14 is a cross-sectional view taken along line XIV-XIV in FIG. 13. As illustrated in FIG. 13 and FIG. 14, the seal member 112 extends from the distal end of the movable cylindrical portion 43 (the distal end of the sheath 31) toward the proximal direction side. The seal member 112 is formed of a resin with high heat resistance, such as PTFE or PEEK. In this modification, liquid tightness between the outer peripheral surface of the multi-lumen tube 80 and the movable cylindrical portion 43 is kept by the seal member 112. Thus, in the distal portion of the cavity portion 45, liquid tightness between the movable cylindrical portion (energy transmission portion) 43 and probe 32 in the outside of the liquid feed conduit 86 is kept by the seal member 112 (and multi-lumen tube 80). Thereby, in the outside of the liquid feed conduit 86, the inflow of liquid into the cavity portion 45 is prevented.

By virtue of the above-described configuration, in the present modification, even if the liquid flowing from the liquid outflow portion 108 (65A, 65B, 66A, 66B) flows to the proximal direction side, the inflow of liquid into the cavity portion 45 in the outside of the liquid feed conduit 86 is prevented by the seal member 112. Thus, the flow of high-frequency current between the movable cylindrical portion 43 and probe 32 via the liquid in the cavity portion 45 (i.e. short-circuit) is prevented. Thereby, the treatment performance in the treatment can be secured.

In the meantime, also in the configuration in which the tube member 102, in place of the multi-lumen tube 80, extends in the cavity portion 45, as in the second modification (see FIG. 8), a seal member (112) may be provided in the distal portion of the cavity portion 45. In this case, too, in the distal portion of the cavity portion 45, liquid tightness between the movable cylindrical portion (energy transmission portion) 43 and probe 32 in the outside of the liquid feed conduit 86 is kept by the seal member (112). Thereby, in the outside of the liquid feed conduit 86, the inflow of liquid into the cavity portion 45 is prevented.

Figure 15:
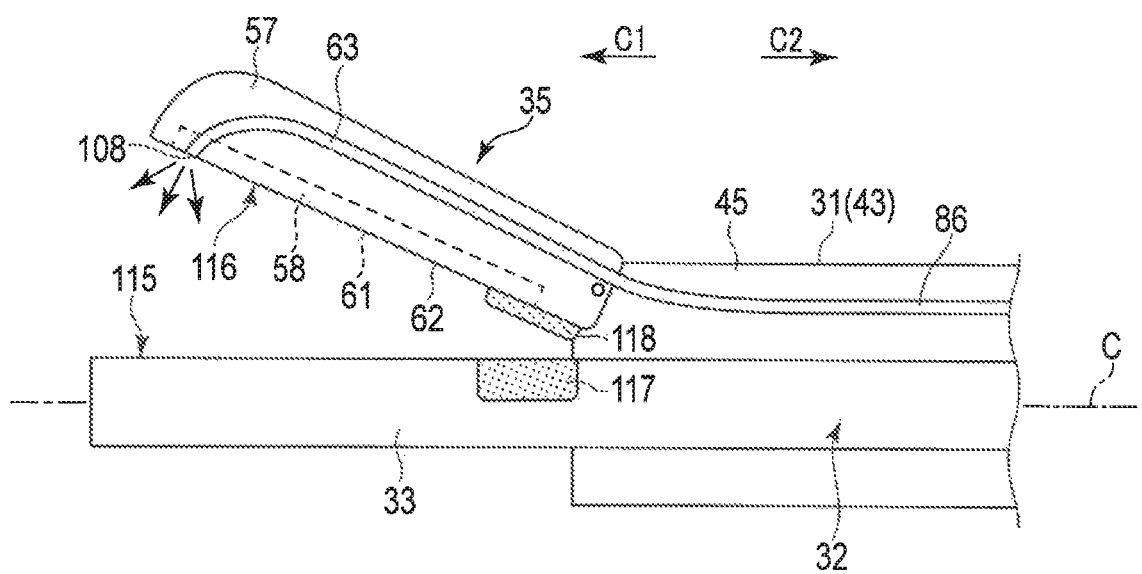
FIG. 15 is a schematic view illustrating the configuration of a distal portion of an energy treatment instrument including a probe distal portion and a jaw according to a sixth modification.
Figure 16:
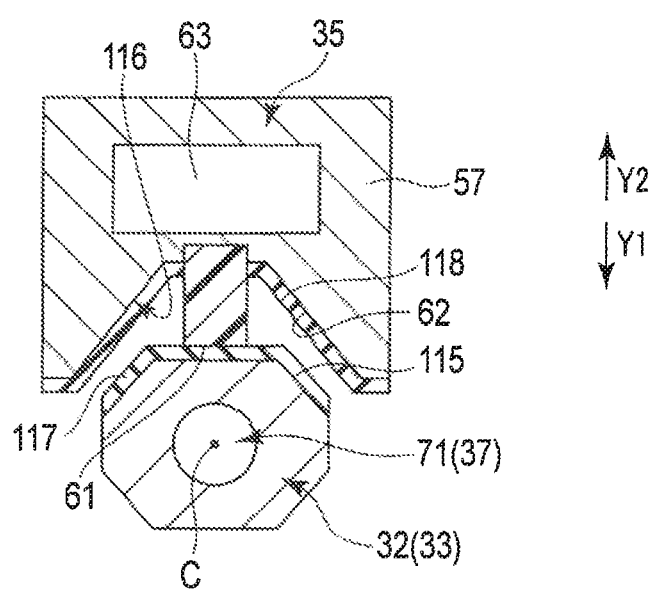
FIG. 16 is a cross-sectional view which schematically illustrates, in cross section perpendicular to a longitudinal axis, the probe distal portion and the jaw according to the sixth modification.

Additionally, a sixth modification will be described with reference to FIG. 15 and FIG. 16. Here, FIG. 15 illustrates the configuration of a distal portion of an energy treatment instrument 2, and FIG. 16 illustrates a cross section perpendicular to the longitudinal axis C of a probe distal portion 33 and a jaw 35. As illustrated in FIG. 15 and FIG. 16, in the present modification, too, liquid flows from the liquid feed conduit 86 into the jaw cavity 63 in the inside of the jaw 35, and the liquid flows to the outside of the jaw 35 from the jaw cavity 63 at the liquid outflow portion 108. In addition, the outer surface of the probe distal portion 33 includes a probe counter-surface 115 which is opposed to the jaw 35, and the outer surface of the jaw 35 includes a jaw counter-surface 116 which is opposed to the probe distal portion 33. In the present modification, the jaw counter-surface 116 is formed by the abutment surface 61 of the pad member 58 and an electrode counter-surface 62 which is opposed to the probe distal portion 33 in the electrode member 57.

In the present modification, a probe coating portion 117 is coated on a proximal-direction-side part of the probe counter-surface 115. Specifically, the probe coating portion 117 is coated on the proximal-direction-side part of the probe distal portion 33 (the projection portion of the probe 32 from the sheath 31). In addition, a jaw coating portion 118 is coated on a proximal-direction-side part of the electrode counter-surface 62. The probe coating portion 117 and jaw coating portion 118 are formed on the proximal direction side with respect to the liquid outflow portion 108 of the jaw cavity 63. Besides, the probe coating portion 117 and jaw coating portion 118 are formed of a material having at least one of electrical insulativeness and water repellency. Here, in FIG. 15, the probe coating portion 117 and jaw coating portion 118 are shown by dotted hatching.

In the bipolar treatment in which a high-frequency current is caused to flow in the treated target via the liquid between the probe distal portion 33 and the electrode member 57 of the jaw 35, there is a case in which the treatment is performed by putting only a distal-direction-side part of the probe counter-surface 115 and a distal-direction-side part of the jaw counter-surface 116 in contact with the treated target. In this case, a proximal-direction-side part of the probe counter-surface 115 and a proximal-direction-side part of the jaw counter-surface 116 are not put in contact with the treated target. As described above, in the bipolar treatment, depending on the attitude of the energy treatment instrument 2, there is a possibility that the liquid flowing from the liquid outflow portion 108 to the outside of the jaw 35 flows to the proximal direction side via the outer surface of the probe distal portion 33.

In the present modification, on the proximal direction side with respect to the liquid outflow portion 108 from which the liquid is caused to flow to the outside of the jaw 35, the probe coating portion 117 is coated on the probe counter-surface 115 (the outer surface of the probe distal portion 33), and the jaw coating portion 118 is coated on the electrode counter-surface 62 of the jaw counter-surface 116. Since the probe coating portion 117 and jaw coating portion 118 are formed of the material with electrical insulativeness, even if liquid adheres to the proximal-direction-side part of the probe counter-surface 115 and the proximal-direction-side part of the jaw counter-surface 116, the flow of high-frequency current via the liquid (i.e. short-circuit) is prevented between the proximal-direction-side part of the probe counter-surface 115 and the proximal-direction-side part of the jaw counter-surface 116.

Since the probe coating portion 117 and jaw coating portion 118 are formed of the material with electrical insulativeness, even if the liquid flowing out of the liquid outflow portion 108 flows to the proximal direction side, the liquid hardly adheres to the proximal-direction-side part of the probe counter-surface 115 and the proximal-direction-side part of the jaw counter-surface 116. Thereby, the flow of high-frequency current via the liquid (i.e. short-circuit) is prevented between the proximal-direction-side part of the probe counter-surface 115 and the proximal-direction-side part of the jaw counter-surface 116.

Additionally, in a certain modification, a probe bend portion, which bends in a certain direction crossing the straight longitudinal axis C, may be provided in the probe distal portion 33 of the probe 32, and a jaw bend portion, which bends in accordance with the probe bend portion, may be provided in the jaw 35. In this case, like the above-described embodiment, etc., the liquid ejected from the jaw ejection port 87 of the liquid feed conduit 86 flows into the jaw cavity 63 in the inside of the jaw 35. Then, the liquid flows to the outside of the jaw 35 from the jaw cavity 63, at the position located on the jaw opening direction side with respect to the abutment surface 61 of the jaw 35 and located on the distal direction side with respect to the proximal end E1 of the abutment surface 61.

Additionally, in a certain modification, the probe 32 may not transmit ultrasonic vibration, and only high-frequency electric power may be supplied as energy to the probe distal portion 33 and the electrode member 57 of the jaw 35. In this case, a bipolar treatment is performed with the probe distal portion 33 and the electrode member 57 of the jaw 35 functioning as electrodes, while liquid is being supplied to the treated target which is grasped between the probe distal portion 33 and the jaw 35.

In the above-described embodiment, etc., a cavity portion (45), through which a probe (32) is inserted, is formed in an inside of an energy transmission portion (43) along a longitudinal axis (C). A jaw (35) is attached to a distal portion of the energy transmission portion (43), and is openable and closable relative to a probe distal portion (33). In addition, the jaw (35) is provided with an abutment surface (61) which is abuttable on the probe distal portion (33) in a state in which the jaw (35) is closed relative to the probe distal portion (33). A jaw cavity (63) is formed in an inside of the jaw (35). Besides, in the cavity portion (45), a liquid feed conduit (86) extends from a proximal direction side toward a distal direction side, through between the energy transmission portion (43) and the probe (32). An ejection port (87) is formed at a distal end of the liquid feed conduit (86). A liquid supplied through the liquid feed conduit (86) is ejected from the ejection port (87) toward the distal direction side, and flows into the jaw cavity (63). A liquid outflow portion (65A, 65B, 66A, 66B; 103A, 103B; 108) is provided on an outer surface of the jaw (35), at a position located on a jaw opening direction side with respect to the abutment surface (61) and located on the distal direction side with respect to a proximal end (E1) of the abutment surface (61). The liquid flowing into the jaw cavity (63) flows to an outside of the jaw (35) from the liquid outflow portion (65A, 65B, 66A, 66B; 103A, 103B; 108).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An energy treatment instrument comprising:
    a probe including a treatment section in a distal portion thereof;
    a sheath configured such that a cavity portion, through which the probe is inserted, is formed in an inside of the sheath;
    a jaw rotatably attached to the sheath, and configured to be openable and closable relative to the treatment section, the jaw further being configured such that a jaw cavity is formed in an inside of the jaw, the jaw including:
        an abutment surface which is abuttable on the treatment section,
        a jaw support portion attached to a distal portion of the sheath, and
        a jaw swing portion swingably attached to the jaw support portion on a jaw closing direction side of the jaw support portion, the jaw swing portion being configured such that the abutment surface is provided on the jaw swing portion and the jaw cavity is formed between the jaw swing portion and the jaw support portion in a jaw closing direction and a jaw opening direction;
    a liquid feed conduit configured to communicate with the jaw cavity, and to cause a supplied liquid to flow into the jaw cavity;
    a liquid outflow portion configured to make the jaw cavity open to an outside of the jaw at a position located on a distal direction side with respect to a proximal end of the abutment surface, and to cause the liquid, which flows into the jaw cavity from the liquid feed conduit, to flow out toward a treatment section side; and
    a collision wall provided in the jaw, and configured such that the liquid flowing in the jaw cavity collides with the collision wall, and thereby the collision wall prevents outflow of the liquid to the outside of the jaw from a region located on a proximal direction side with respect to the proximal end of the abutment surface.

2. The energy treatment instrument of claim 1, further comprising a tube member extending from the proximal direction side toward the distal direction side in the cavity portion, the tube member being configured such that the liquid feed conduit extends through an inside of the tube member.

3. The energy treatment instrument of claim 1, wherein a distal end of the liquid feed conduit communicates directly with a proximal end of the jaw cavity.

4. The energy treatment instrument of claim 1, wherein the jaw swing portion includes:
    a pad member formed of an electrically insulative material, the pad member being provided with the abutment surface; and
    an electrode member formed of an electrically conductive material, the electrode member being configured such that a gap is formed between the electrode member and the treatment section in a state in which the abutment surface abuts on the treatment section, and configured to function as an electrode by being supplied with a high-frequency electric power.

5. The energy treatment instrument of claim 1, further comprising a gas feed conduit extending through an inside of the jaw in a state in which the gas feed conduit is isolated from the jaw cavity and the liquid feed conduit, the gas feed conduit including a gas ejection port located on the proximal direction side with respect to the liquid outflow portion on an outer surface of the jaw, and the gas feed conduit being configured to eject a gas from the gas ejection port to the outside of the jaw toward the treatment section.

6. The energy treatment instrument of claim 1, further comprising a seal member configured to keep liquid tightness between the sheath and the probe in an outside of the liquid feed conduit in a distal portion of the cavity portion formed in the inside of the sheath, thereby preventing inflow of the liquid into the cavity portion from the distal direction side in the outside of the liquid feed conduit.

7. The energy treatment instrument of claim 1, further comprising a suction conduit extending from the proximal direction side toward the distal direction side in an inside of the probe, the suction conduit being configured to be open to an outside of the probe at an opening portion located on an outer surface of the treatment section, and to perform suction through the opening portion.

8. The energy treatment instrument of claim 1, wherein the probe is configured to transmit high-frequency electric power as energy for use in a treatment from the proximal direction side toward the distal direction side, and
the treatment section is configured to function as an electrode, by the high-frequency electric power being supplied to the treatment section.

9. The energy treatment instrument of claim 8, wherein the jaw includes an electrode member formed of an electrically conductive material, the electrode member being configured such that a gap is formed between the electrode member and the treatment section in a state in which the abutment surface abuts on the treatment section, and configured to function as an electrode by being supplied with the high-frequency electric power as the energy,
the electrode member includes an electrode counter-surface which is opposed to the treatment section, and
the energy treatment instrument further includes a coating portion coated on an outer surface of the treatment section and on the electrode counter-surface of the electrode member in a region located on the proximal direction side with respect to the liquid outflow portion, the coating portion being formed of a material having at least one of electrical insulativeness and water repellency.

10. The energy treatment instrument of claim 1, further comprising a vibration generating section configured to generate ultrasonic vibration as energy for use in a treatment,
wherein the probe is configured to transmit the generated ultrasonic vibration to the treatment section from the proximal direction side toward the distal direction side.

11. The energy treatment instrument of claim 4, wherein a hole-shaped portion, which penetrates the electrode member, is formed in the electrode member, and
the liquid outflow portion is provided in the hole-shaped portion.

12. An energy treatment instrument comprising:
a probe including a treatment section in a distal portion thereof;
a sheath configured such that a cavity portion, through which the probe is inserted, is formed in an inside of the sheath;
a jaw rotatably attached to the sheath, and configured to be openable and closable relative to the treatment section, the jaw including an abutment surface which is abuttable on the treatment section, and the jaw being configured such that a jaw cavity is formed in an inside of the jaw;
a liquid feed conduit configured to communicate with the jaw cavity, and to cause a supplied liquid to flow into the jaw cavity;
a multi-lumen tube extending from a proximal direction side toward a distal direction side in the cavity portion, the multi-lumen tube being configured such that a first lumen and a second lumen are formed from the proximal direction side toward the distal direction side in a state in which the first lumen and the second lumen are isolated from each other, and the multi-lumen tube being configured such that the liquid feed conduit extends through the first lumen, and the probe is inserted through the second lumen; and
a liquid outflow portion configured to make the jaw cavity open to an outside of the jaw at a position located on the distal direction side with respect to a proximal end of the abutment surface, and to cause the liquid, which flows into the jaw cavity from the liquid feed conduit, to flow out toward a treatment section side.

13. The energy treatment instrument of claim 12, further comprising a connection tube having a proximal end connected to the multi-lumen tube at a distal end of the first lumen, and having a distal end connected to the jaw, the connection tube being configured such that the liquid feed conduit extends in an inside of the connection tube, and the connection tube being configured to eject the liquid, which is supplied through the liquid feed conduit, from the distal end toward the jaw cavity.

14. The energy treatment instrument of claim 12, wherein the multi-lumen tube includes:
a tube base surface on which a distal end of the second lumen is located, and which faces toward the distal direction side; and
a tube projection portion projecting from the tube base surface toward the distal direction side, the tube projection portion being configured such that the first lumen extends through an inside of the tube projection portion, a distal end of the tube projection portion is connected to the jaw, and the projection portion being configured to eject the liquid, which is supplied through the liquid feed conduit, from the distal end toward the jaw cavity.

* * * * *